US012121325B2

(12) United States Patent
Schmitt et al.

(10) Patent No.: US 12,121,325 B2
(45) Date of Patent: Oct. 22, 2024

(54) LUMEN MORPHOLOGY AND VASCULAR RESISTANCE MEASUREMENTS DATA COLLECTION SYSTEMS APPARATUS AND METHODS

(71) Applicant: LightLab Imaging, Inc., Westford, MA (US)

(72) Inventors: Joseph M. Schmitt, Andover, MA (US); Joel M. Friedman, Andover, MA (US); Christopher Petroff, Groton, MA (US); Amr Elbasiony, Chelmsford, MA (US)

(73) Assignee: LightLab Imaging, Inc., Westford, MA (US)

( * ) Notice: Subject to any disclaimer, the term of this patent is extended or adjusted under 35 U.S.C. 154(b) by 0 days.

(21) Appl. No.: 17/508,272

(22) Filed: Oct. 22, 2021

(65) Prior Publication Data

US 2022/0095934 A1   Mar. 31, 2022

Related U.S. Application Data

(63) Continuation of application No. 16/549,814, filed on Aug. 23, 2019, which is a continuation of application
(Continued)

(51) Int. Cl.
*A61B 5/02* (2006.01)
*A61B 5/00* (2006.01)

(52) U.S. Cl.
CPC ........ *A61B 5/02007* (2013.01); *A61B 5/0066* (2013.01); *A61B 5/0073* (2013.01); *A61B 5/0084* (2013.01)

(58) Field of Classification Search
CPC . A61B 5/02007; A61B 5/0066; A61B 5/0073; A61B 5/0084
See application file for complete search history.

(56) References Cited

U.S. PATENT DOCUMENTS 5,054,492 A   10/1991 Scribner et al.
5,321,501 A   6/1994 Swanson et al.
(Continued)

FOREIGN PATENT DOCUMENTS

EP   2062526 A1   5/2009
JP   H05064638 A   3/1993
(Continued)

OTHER PUBLICATIONS

Pim A.L. Tonino, "Fractional Flow Reserve versus Angiography for Guiding Percutaneous Coronary Intervention, [Jan. 15, 2009], N Engl J Med 2009." (Year: 2009).*
(Continued)

*Primary Examiner* — Boniface N Nganga
*Assistant Examiner* — Zainab Mohammed Aldarraji
(74) *Attorney, Agent, or Firm* — Lerner David LLP

(57) ABSTRACT

A method and apparatus of automatically locating in an image of a blood vessel the lumen boundary at a position in the vessel and from that measuring the diameter of the vessel. From the diameter of the vessel and estimated blood flow rate, a number of clinically significant physiological parameters are then determined and various user displays of interest generated. One use of these images and parameters is to aid the clinician in the placement of a stent. The system, in one embodiment, uses these measurements to allow the clinician to simulate the placement of a stent and to determine the effect of the placement. In addition, from these patient parameters various patient treatments are then performed.

24 Claims, 24 Drawing Sheets

Related U.S. Application Data

No. 13/796,710, filed on Mar. 12, 2013, which is a continuation of application No. 12/888,347, filed on Sep. 22, 2010, now Pat. No. 9,138,147.

(60) Provisional application No. 61/334,834, filed on May 14, 2010, provisional application No. 61/244,992, filed on Sep. 23, 2009.

(56) References Cited

U.S. PATENT DOCUMENTS

| | | |
|---|---|---|
| 5,357,550 A | 10/1994 | Asahina et al. |
| 5,459,570 A | 10/1995 | Swanson et al. |
| 5,465,147 A | 11/1995 | Swanson |
| 5,488,674 A | 1/1996 | Burt et al. |
| 5,509,093 A | 4/1996 | Miller et al. |
| 5,531,227 A | 7/1996 | Schneider |
| 5,619,368 A | 4/1997 | Swanson |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,956,355 A | 9/1999 | Swanson et al. |
| 5,965,355 A | 10/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,208,883 B1 | 3/2001 | Holupka et al. |
| 6,282,011 B1 | 8/2001 | Tearney et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,585,660 B2 | 7/2003 | Dorando et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,947,040 B2 | 9/2005 | Tek et al. |
| 7,134,994 B2 | 11/2006 | Alpert et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,329,223 B1 | 2/2008 | Ainsworth et al. |
| 7,359,554 B2 | 4/2008 | Klingensmith et al. |
| 7,414,779 B2 | 8/2008 | Huber et al. |
| 7,415,049 B2 | 8/2008 | Flanders et al. |
| 7,450,241 B2 | 11/2008 | Zuluaga |
| 7,532,920 B1 | 5/2009 | Ainsworth et al. |
| 7,593,559 B2 | 9/2009 | Toth et al. |
| 7,610,081 B2 | 10/2009 | Redel |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,706,585 B2 | 4/2010 | Kleen |
| 7,729,746 B2 | 6/2010 | Redel et al. |
| 7,733,497 B2 | 6/2010 | Yun et al. |
| 7,783,338 B2 | 8/2010 | Ainsworth et al. |
| 7,785,286 B2 | 8/2010 | Magnin et al. |
| 7,794,230 B2 * | 9/2010 | Lakin .................. G09B 23/12 |
| | | 434/270 |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,872,759 B2 | 1/2011 | Tearney et al. |
| 7,916,387 B2 | 3/2011 | Schmitt |
| 7,930,014 B2 | 4/2011 | Huennekens et al. |
| 7,935,060 B2 | 5/2011 | Schmitt et al. |
| 8,029,447 B2 | 10/2011 | Kanz et al. |
| 8,116,605 B2 | 2/2012 | Petersen et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,478,387 B2 | 7/2013 | Xu |
| 11,185,368 B2 | 11/2021 | Spilker et al. |
| 2002/0049375 A1 | 4/2002 | Strommer et al. |
| 2002/0115931 A1 | 8/2002 | Strauss et al. |
| 2002/0161351 A1 | 10/2002 | Samson et al. |
| 2002/0173724 A1 | 11/2002 | Dorando et al. |
| 2003/0023266 A1 | 1/2003 | Borillo et al. |
| 2003/0032886 A1 | 2/2003 | Dgany et al. |
| 2003/0204160 A1 * | 10/2003 | Kamm .................. A61F 2/2493 |
| | | 604/8 |
| 2004/0049115 A1 | 3/2004 | Murphy et al. |
| 2004/0236230 A1 | 11/2004 | Crowley et al. |
| 2004/0249270 A1 | 12/2004 | Kondo et al. |
| 2005/0043609 A1 | 2/2005 | Murphy et al. |
| 2005/0201662 A1 | 9/2005 | Petersen et al. |
| 2005/0249391 A1 | 11/2005 | Kimmel et al. |
| 2005/0267379 A1 | 12/2005 | Pfeiffer et al. |
| 2005/0272992 A1 | 12/2005 | O'Donnell et al. |
| 2005/0288577 A1 | 12/2005 | Weese |
| 2006/0052700 A1 | 3/2006 | Svanerudh |
| 2006/0079782 A1 * | 4/2006 | Beach ................. G01S 7/52026 |
| | | 600/450 |
| 2006/0095065 A1 | 5/2006 | Tanimura et al. |
| 2006/0127867 A1 | 6/2006 | Grund-Pedersen |
| 2006/0135870 A1 | 6/2006 | Webler |
| 2006/0165270 A1 | 7/2006 | Borgert et al. |
| 2006/0166176 A1 * | 7/2006 | Lakin ..................... G09B 23/12 |
| | | 434/262 |
| 2006/0235669 A1 | 10/2006 | Charbel et al. |
| 2006/0241342 A1 | 10/2006 | Macaulay et al. |
| 2006/0241465 A1 | 10/2006 | Huennekens et al. |
| 2006/0241469 A1 | 10/2006 | Rold et al. |
| 2007/0038061 A1 * | 2/2007 | Huennekens ............ A61B 8/12 |
| | | 600/407 |
| 2007/0060822 A1 | 3/2007 | Alpert et al. |
| 2007/0135707 A1 | 6/2007 | Redel et al. |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2008/0004530 A1 | 1/2008 | Feldman et al. |
| 2008/0040087 A1 * | 2/2008 | Watrous .................. A61B 7/02 |
| | | 703/11 |
| 2008/0075375 A1 | 3/2008 | Unal et al. |
| 2008/0228086 A1 | 9/2008 | Ilegbusi et al. |
| 2008/0269572 A1 | 10/2008 | Kanz et al. |
| 2008/0281205 A1 | 11/2008 | Naghavi et al. |
| 2008/0294038 A1 * | 11/2008 | Weese .................. A61B 6/507 |
| | | 600/431 |
| 2009/0143686 A1 | 6/2009 | Onimura et al. |
| 2009/0177454 A1 | 7/2009 | Bronstein et al. |
| 2009/0182409 A1 | 7/2009 | Feld et al. |
| 2009/0262361 A1 | 10/2009 | Tanioka et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0253949 A1 | 10/2010 | Adler et al. |
| 2010/0290693 A1 | 11/2010 | Cohen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2012/0041739 A1 * | 2/2012 | Taylor ..................... A61B 6/03 |
| | | 703/11 |

(56) References Cited

U.S. PATENT DOCUMENTS

| | | |
|---|---|---|
| 2013/0030295 A1 | 1/2013 | Huennekens et al. |
| 2019/0365336 A1 | 12/2019 | Wagner et al. |
| 2021/0219924 A1 | 7/2021 | Liberson et al. |
| 2021/0280993 A1* | 9/2021 | Murray ............... H01R 4/2433 |
| 2021/0319558 A1 | 10/2021 | Min et al. |
| 2021/0353160 A1* | 11/2021 | Laleg .................... A61B 5/026 |
| 2022/0039667 A1 | 2/2022 | Schmitt et al. |

FOREIGN PATENT DOCUMENTS

| | | | |
|---|---|---|---|
| JP | 2001-079097 | A | 3/2001 |
| JP | 2003525067 | A | 8/2003 |
| JP | 2003527164 | A | 9/2003 |
| JP | 2004-510515 | A | 4/2004 |
| JP | 2004528920 | A | 9/2004 |
| JP | 2004283373 | A | 10/2004 |
| JP | 2006508731 | A | 3/2006 |
| JP | 2006509239 | A | 3/2006 |
| JP | 2007-502676 | A | 2/2007 |
| JP | 2007135894 | A | 6/2007 |
| JP | 2007-526083 | A | 9/2007 |
| JP | 2008514303 | A | 5/2008 |
| JP | 2008523954 | A | 7/2008 |
| JP | 2008531200 | A | 8/2008 |
| JP | 2008543511 | A | 12/2008 |
| JP | 200918184 | A | 1/2009 |
| JP | 2009022733 | A | 2/2009 |
| JP | 2009-125394 | A | 6/2009 |
| JP | 2009128074 | A | 6/2009 |
| JP | 2009213617 | A | 9/2009 |
| WO | 0141638 | A1 | 6/2001 |
| WO | 02094339 | A2 | 11/2002 |
| WO | 2004051579 | A2 | 6/2004 |
| WO | 2004051604 | A1 | 6/2004 |
| WO | 2006037001 | A1 | 4/2006 |
| WO | 2006076409 | A2 | 7/2006 |
| WO | 2007002685 | A2 | 1/2007 |
| WO | 2011003013 | A2 | 1/2011 |

OTHER PUBLICATIONS

Catherine M. Otto, "Valvular Aortic Stenosis: Disease Severity and Timing of Intervention, [May 15, 2005], JACC Journals, vol. 47 No. 11" (Year: 2005).*

Mette S. Olufsen, "Structured tree outflow condition for blood flow in larger systemic arteries, [Jan. 1, 1999], vol. 276 Issue 1 Jan. 1999, pp. H257-H268" (Year: 1999).*

Leonardo Flórez-Valencia ("3D graphical models for vascular-stent pose simulation", [Apr. 26, 2012]) (Year: 2012).*

Jeroen P., Model prediction of subendocardial perfusion of the coronary circulation in the presence of an epicardial coronary artery stenosis, Feb. 2008, Med Biol Eng Comput) (Year: 2008).*

Ivaro Valencia, Numerical simulation of fluid-structure interaction in stenotic arteries considering two layer nonlinear anisotropic structural model, International Communications in Heat and Mass Transfer,vol. 36, Issue 2, (Year: 2009).*

Banerjee, R.K., Ashtekar, K.D., Helmy, T.A. et al. Hemodynamic diagnostics of epicardial coronary stenoses: in-vitro experimental and computational study. BioMed Eng Online 7, 24 (2008). https://doi.org/10.1186/1475-925X-7-24 (Year: 2008).*

Appanaboyina, S., Castro, M. A., Lohner, R., & Cebral, J. R. (2005). Simulation of endovascular interventions of cerebral aneurysms: Techniques and evaluation. SPIE Proceedings. https://doi.org/10.1117/12.593901 (Year: 2005).*

Barlis, Et al., "The Use of Intracoronary Optical Coherence Tomography in Interventional Cardiology: Saety, Feasibility and Clinical Applications", 368 pages, 2009.

Boutsianis, E. et al., "Computational simulation of intracoronary flow based on real coronary geometry," European Journal of Cardiothoracic Surgery, Apr. 2004, pp. 248-256, vol. 26, Elsevier.

Ellwein, L. M. et al., "Sensitivity Analysis and Model Assessment: Mathematical Models for Arterial Blood Flow and Blood Pressure," Cardiovasc Eng, Dec. 2007, pp. 94-108, vol. 8, Springer.

Spilker, R.L. et al., "Morphometry-Based Impedance Boundary Conditions for Patient-Specific Modeling of Blood Flow in Pulmonary Arteries," Annals of Biomedical Engineering, Apr. 2007, pp. 546-559, vol. 35, No. 4, Biomedical Engineering Society.

Taylor, C.A. et al., "open problems in computational vascular biomechanics:hemodynamics and arterial wall mechanics," NIH Public Access, Sep. 2009, pp. 1-19, vol. 198.

Taylor, C.A. et al., "Patient-specific Modeling of Cardiovascular Mechanics," HHS Public Access, Sep. 2015, pp. 1-31, vol. 11.

Ofili et al. ("Differential characterization of blood flow, velocity, and vascular resistance between proximal and distal normal epicardial human coronary arteries: Analysis by intracoronary Doppler spectral flow velocity", [Jul. 1995]) (Year: 1995).

LaDisa et al., "Circumferential vascular deformation after stent implantation alters wall shear stress evaluated with time dependent 3D computational fluid dynamics models", [Mar. 2005] (Year:2005).

Verhoeff, "influence of percutaneous coronary intervention on coronary microvascular resistance index", [Dec. 2004] (Year: 2004).

Maartje CF Geven et al, A physiologically representative in vitro model of the coronary circulation, 2004 Physiol. Meas. 25 891. (Dec. 2003). 15 pgs.

M. Siebes and J. J. Piek, "Mathematical model of pressure-related changes in coronary diameter and their effect on the assessment of coronary flow velocity reserve," Engineering in Medicine and Biology Society. (Jul. 2000). 2 pgs.

Cebral, Juan & Lohner, Rainald & Soto, Orlando & Choyke, Peter & Yim, Peter. (2001). Patient-Specific Simulation of Carotid Artery Stenting Using Computational Fluid Dynamics. 153-160. 10.1007/3-540-45468-3_19. (Year: 2001).

Samady H, Baseline fractional flow reserve and stent diameter predict optimal post-stent fractional flow reserve and major adverse cardiac events after bare-metal stent deployment. JACC Cardiovasc Interv. Apr. 2009; (Year: 2009).

Quatember, Bernhard & Mayr, Martin & Recheis, Wolfgang. (2008). Patient-specific modelling and simulation of coronary haemodynamics. Proceedings of the 2008 Spring Simulation Multiconference, SpringSim'08. 573-580. 10.1145/1400549.1400639. (Year:2008).

Holzapfel, G. A., Stadler, M., and Gasser, T. C. (Mar. 8, 2005). "Changes in the Mechanical Environment of Stenotic Arteries During Interaction With Stents: Computational Assessment of Parametric Stent Designs." ASME. J Biomech Eng. Feb. 2005 (Year: 2005).

Ashley WW, Amin-Hanjani S, Alaraj A, Shin JH, Charbel FT, Flow-assisted surgical cerebral revascularization. Neurosurg Focus, Feb. 2008; pp. 1-12, 24(2):E20.doi: 10.3171/FOC/2008/24/2/E20. PMID: 18336091. (Year: 2008).

Meuwissen, Martijn, "Role of variability in microvascular resistance on fractional flow reserve and coronary blood flow velocity reserve in intermediate coronary lesions", Jan. 2001, Circulation, vol. 103, pp. 184-187.

Sihan K et al: "A novel approach to quantitative analysis of intravascular optical coherence tomography imaging", Computers in Cardiology, 2008, IEEE, Piscataway, NJ, USA, Sep. 14, 2008 (Sep. 14, 2008 ), pp. 1089-1092, XP0314067 48, ISBN: 978-1-4244-3706-1.

Tearney, et al., "Three-Dimensional Coronary Artery Microscopy by Intracoronary Optical Frequency Domain Imaging," JACC: Cardiovascular Imaging, 2008 by the American College of Cardiology Foundation, vol. 1, No. 6, Jun. 2008, pp. 752-761.

Tyml K, Anderson D, Lidington D, Ladak HM. A new method for assessing arteriolar diameter and hemodynamic resistance using image analysis of vessel lumen. Am J Physiol Heart Circ Physiol. May 2003;284(5):H1721-8. doi: 10.1152/ajpheart.00741.2002. Epub Jan. 9, 2003. PMID: 12521937. ( Jan. 2003). 8 pgs.

Decision to Grant a Patent for Japanese Application No. 2020-203808 dated Nov. 1, 2022. 3 pgs.

George C. Kagadis, Computational representation and hemodynamic characterization of in vivo acquired severe stenotic renal artery geometries using turbulence modeling, Medical Engineering & Physics,vol. 30, Issue 5, 2008 (Jul. 2007).

(56) References Cited

OTHER PUBLICATIONS

John F. LaDisa, Jr, Stent design properties and deployment ratio influence indexes of wall shear stress: a three-dimensional computational fluid dynamics investigation within a normal artery, Journal of Applied Physiology, Feb. 2004 97:1, 424-430 (Year: 2004).
Office Action for European Application No. 14151395.2 dated Dec. 2, 2022. 6 pgs.
Sunil Appanaboyina,"Simulation of endovascular interventions of cerebral aneurysms: techniques and evaluation," Proc. SPIE 5746, Medical Imaging 2005: Physiology, Function, and Structure from Medical Images, (Apr. 14, 2005); doi: (Year: 2005).
Taylor, Charles A., et al. "Predictive medicine: computational techniques in therapeutic decision-making." ComputerAided Surgery: Official Journal of the International Society for Computer Aided Surgery (ISCAS) 4.5 (Dec. 1999): 231-247. (Year: 1999).
Verburg, M., et al. "A lumped parameter model of coronary flow to analyze time intensity curves extracted from angiograms." Report No. BMTE 7 (May-Jul. 2007). (Year: 2007).
W. C. K. Wong and A. C. S. Chung, "Augmented vessels for quantitative analysis of vascular abnormalities and endovascular treatment planning," in IEEE Transactions on Medical Imaging, vol. 25, No. 6, pp. 665-684, Jun. 2006, doi: 10.1109/TMI .2006.873300. (Year: 2006).
Carlo Briguori, intravascular ultrasound criteria for the assessment of the functional significance of intermediae coronary artery stenose and comparison with fractional flow reserve, the American Journal of Cardiology, vol. 87, Issue 2, 2001, pp. 136-141, (Year: 2001).
Guagliumi, The Race to Achieve the Gold Standard in Coronary Imaging, Rev Esp Cardiol. 2009;62(6):599-602.
Hau, Routine Pressure-Derived Fractional Flow Reserve Guidance: From Diagnostic to Everyday Practice, Journal of Invasive Cardiology, vol. 18—Issue 5—May 2006.
Kassab et al., "The pattern of coronary arteriolar bifurcations and the uniform shear hypothesis," Annals of Biomedical Engineering 23 (1): 13-20, 1995.
Hariri et al., "An automatic image processing algorithm for initialing and terminating intracoronary OFDI pullback" Biomedical Optics Express 1 :2 566-573 (Sep. 1, 2010).
Harrison et al., "The value of lesion cross-sectional area determined by quantitative coronary angiography in assessing the physiologic significance of proximal left anterior descending coronary arterial stenoses," Circulation 69:6 1111-1119, 1984.
Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.
Kolyva et al., "Increased diastolic lime fraction as beneficial adjunct of a1-adrenergic receptor blockade after percutaneous coronary intervention," Am J Physiol Heart Gire Physiol 295: H2054-H2060, 2008.
Kolyva et al., "'Windkesselness' of coronary arteries hampers assessment of human coronary wave speed by single-point technique," Am J Physiol Heart Gire Physiol, 295: H482-H490, 2008.
Laslett, "Nonnal left main coronary artery diameter can be predicted from diameters of its branch vessels," Clinical Cardiology 18 (10): 580-582, 1995.
Ohta et al., "Rheological Changes After Stenting of a Cerebral Aneurysm: A Finite Element Modeling Approach, "Cardiovascular and Interventional Radiology (2005) 28:768-772.
Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.
Seiler et al., "Basic structure-function relations of the epicardial coronary vascular tree, Basis of quantitative coronary arteriography for diffuse coronary artery disease," Circulation 85 (6): 1987-2003, 1992.
Siebes et al., "Single-wire pressure and ftow velocity measurement to quantify coronary stenosis hemodynamics and effects of percutaneous interventions," Circulation 109:756-762, 2004.
Sihan et al., "Fully Automatic Three-Dimensional Quantitative Analysis of Intracoronary Optical Coherence Tomography: Method and Validation," Catheterization and Cardiovascular Interventions 74:1058-1065 (2009).
Spaan, "Coronary Blood Flow," Ch 12. Dordrecht, The Netherlands: Kluwer Acedemic Publishers, Boston; 1991: pp. 333-361.
Takagi et al., "Clinical potential of intravascular ultrasound for physiological assessment of coronary stenosis," Circulation 100: 250-255, 1999.
Verhoeff et al., "Influence of percutaneous coronary intervention on coronary microvascular resistance index," Circulation 111 :76-82, 2005.
White et al., "Does visual interpretation of the coronary angiogram predict the physiologic importance of coronary stenoses?," N. Engl J Med 310:13 819-824, 1984.
Wilson et al., "Prediction of the physiologic significance of coronary arterial lesions by quantitative lesion geometry in patients with limited coronary artery disease," Circulation 75: 723-732, 1987.
PCT International Search Report and Written Opinion of International Searching Authority for International Patent Application No. PCT/US2010/049887, mailed Jun. 9, 2011, 19 pages.
Herrington et al., "Semi-automated boundary detection for intravascular ultrasound," Computers in Cardiology 1992 Proceedings., pp. 103-106, Oct. 1992.
Sonka et al., "Segmentation of intravascular ultrasound images: a knowledge-based approach," IEEE Transactions on Medical Imaging, 14(4):719-732, Dec. 1995.
Mojsilovic et al., "Automatic segmentation of intravascular ultrasound images: A texture-based approach," Annals of Biomedical Engineering, 25:1059—1071, Nov. 1997.
Gil et al., "Automatic segmentation of artery wall in coronary IVUS images: a probabilistic approach," Computers in Cardiology 2000; 27:687-690.
Haas et al., "Segmentation of 30 intravascular ultrasonic images based on a random field model," Ultrasound in Medicine & Biology, 26:2, 297-306, 2000.
Kovalski et al., "Three-dimensional automatic quantitative analysis of intravascular ultrasound images," Ultrasound in Medicine & Biology, 26(4):527-537, 2000.
Pujol et al., "Intravascular Ultrasound Images Vessel Characterization using AdaBoost," Functional Imaging and Modeling of the Heart: Lecture Notes in Computer Science, pp. 242-251, 2003.
Taki et al., "Automatic segmentation of calcified plaques and vessel borders in IVUS images," International Journal of Computer Assisted Radiology and Surgery, 3(3-4):347-354, Sep. 2008.
Van den Berg et al., "Using three-dimensional rotational angiography for sizing of covered stents," Am. J. Roentgenology, 178:149-152 (2002).
Wong et al., "A novel method of coronary stent sizing using intravascular ultrasound: safety and clinical outcomes," Int J. Angiol. , 18(1): 22-24 2009.
"Bonnema et al; Assessment of blood vessel mimics with optical coherence tomography, Journal of Biomedical Optics 12; 2,024018; Mar./Apr. 2007 (Year: 2007)".
"Namati et al Alveolar Dynamics during Respiration, American Journal of Respiratory Cell and Molecular Biology vol. 38 2008 (Year: 2008)".
Chrzanowski,Intravascular ultrasound assessment of blood vessel morphology, Folia Morphol., vol. 61, No. 4, pp. 309-312.
C7-XR™ OCT Intravascular Imaging System Company product information.
"Virmani et al., Localized Hypersensitivity and Late Coronary Thrombosis Secondary to a Sirolimus-Eluting Stent Should We Be Cautious? Circulation Feb. 17, 2004".
"Sanz et al., Development of Software for Three-Dimensional Reconstruction and Automatic Quantification of Intravascular Ultrasound (IVUS). Initial Experience, Rev Esp Cardiol. 2006;59(9):879-88".
"Pazos et al., Mechanical Characterization of Atherosclerotic Arteries Using Finite-Element Modeling: Feasibility Study on Mock Arteries, IEEE Transactions On Biomedical Engineering, vol. 57, No. 6, Jun. 2010".

(56) References Cited

OTHER PUBLICATIONS

"Olson et al Chord length distributions in binary stochastic media in two and three dimensions, Journal of Quantitative Spectroscopy & Radiative Transfer 101 (2006) 269-283".

Oshima, Intravascular Ultrasound Analysis of the Radial Artery for Coronary Artery Bypass Grafting, Ann Thorac Surg 2005;79:99-103.

"Hahn, Serial Intravascular Ultrasound Analysis of the Main and Side Branches in Bifurcation Lesions Treated With the TStenting Technique, JACC vol. 54, No. 2, Jul. 7, 2009, 2009:110-7".

Japanese Search Report for App No. 2016-155715 dated Apr. 10, 2017, 13 pages.

Japanese Search Report for App No. 2018-011426 dated Nov. 13, 2018, 14 pages.

Japanese Search Report for App No. 2022-208185 dated Nov. 22, 2023, 11 pages.

Japanese Office Action for Application No. 2012531008 mailed Mar. 3, 2015, 4 pages.

JP Office Action issued in Appln. No. 2022-208185 mailed Nov. 21, 2023 (3 pages).

Masaru Aikawa et al., "Influence of the degree and length of stenosis on coronary flow", Journal of Tokyo Medical University, Japan, The Medical Society of Tokyo Medical University, May 1, 1999, vol. 57, No. 3, pp. 219-225.

English translation of Japanese Office Action for JP 2012-531008 mailed Sep. 19, 2013 (5 pages).

English translation of Japanese Office Action for JP 2013-070193 mailed Nov. 5, 2013 (4 pages).

Official Action in respect to US 2014/0276011 dated Aug. 7, 2015. 105 pgs.

Canadian Office Action issued in Appln. No. 2926666 mailed Jan. 25, 2024 (5 pages).

Gonzalo et al.(Quantitative Ex Vivo and In Vivo Comparison of Lumen Dimensions Measured by Optical Coherence Tomography and Intravascular Ultrasound in Human Coronary Arteries; Rev Esp Cardiol. 2009;62(6):615-24 (Year: 2009).

\* cited by examiner

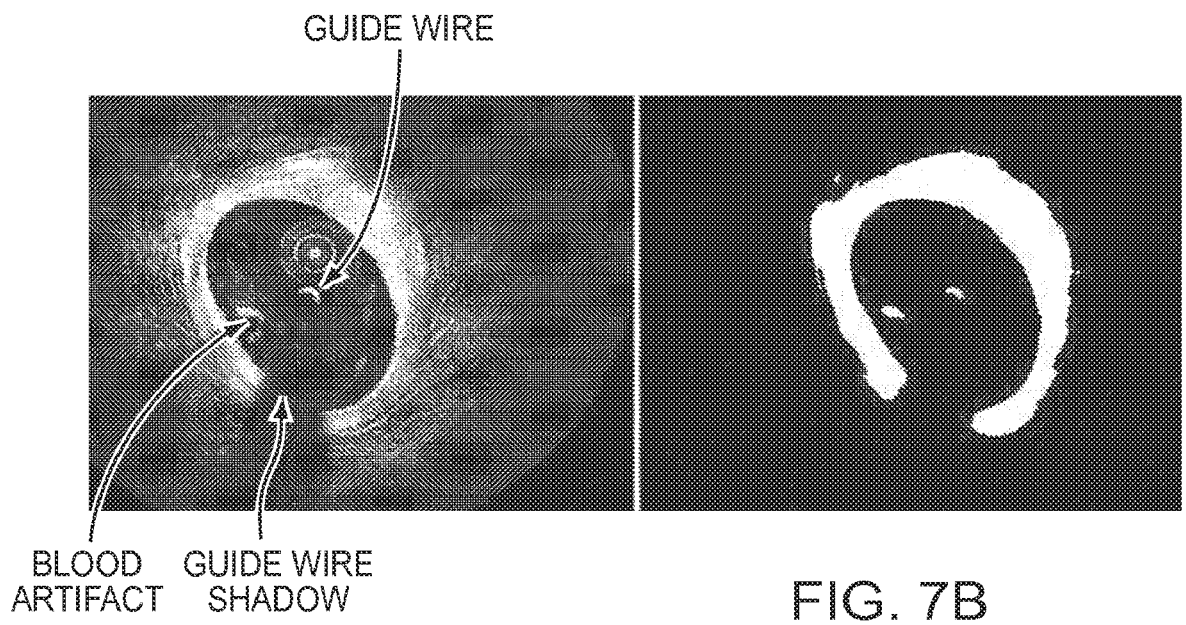
FIG. 7A
FIG. 7B
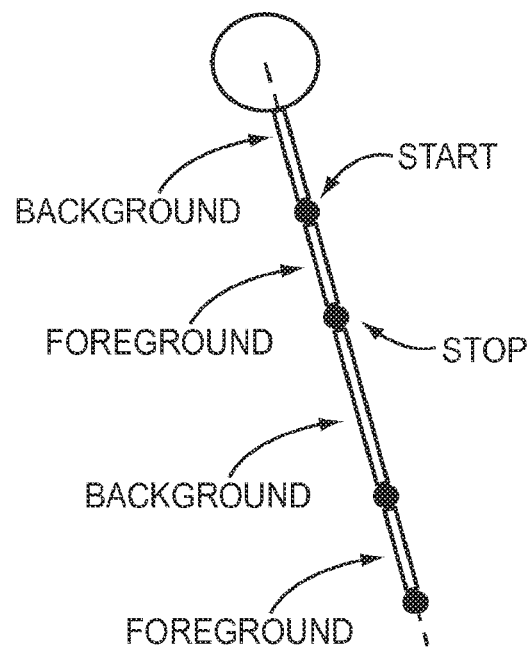
FIG. 8

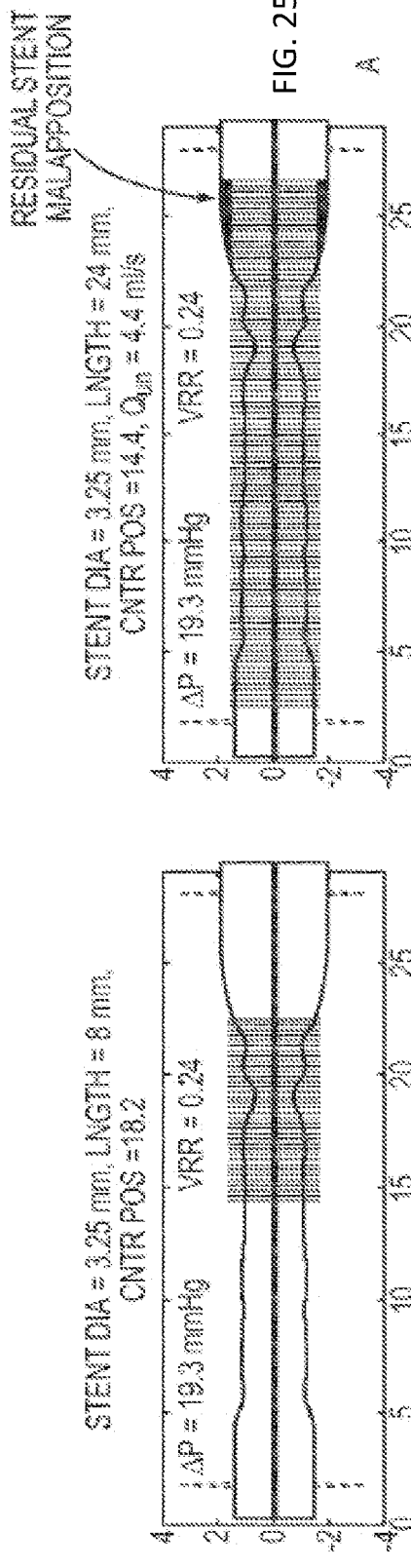
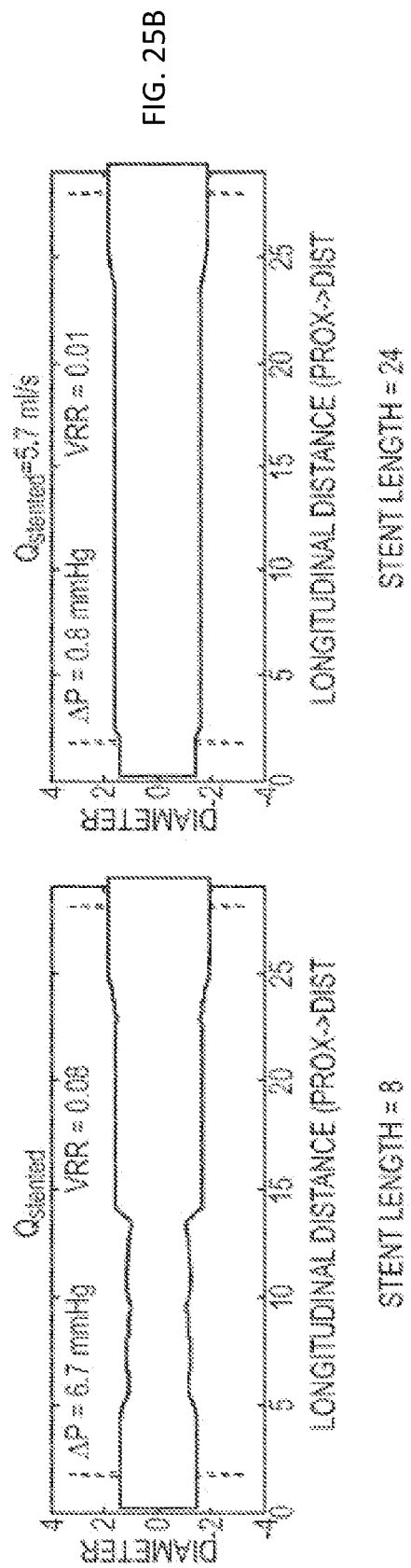
FIG. 25A
FIG. 25B

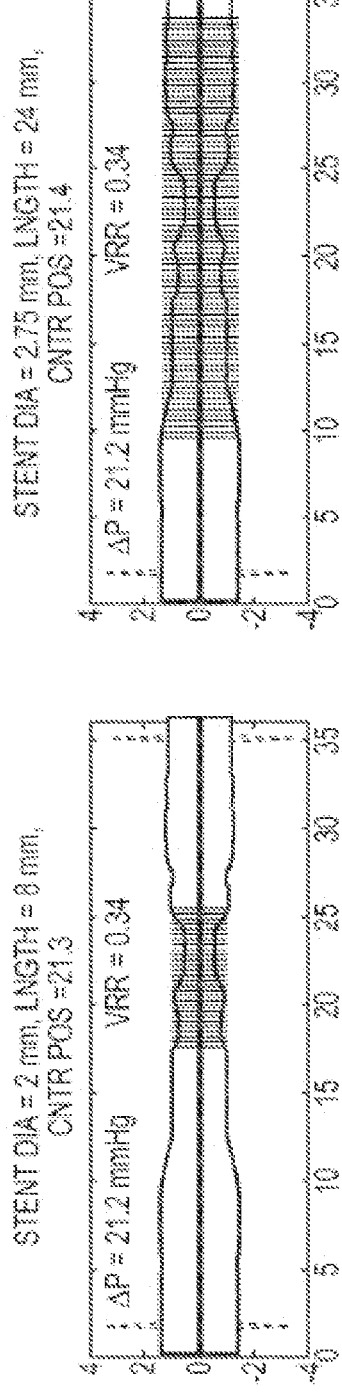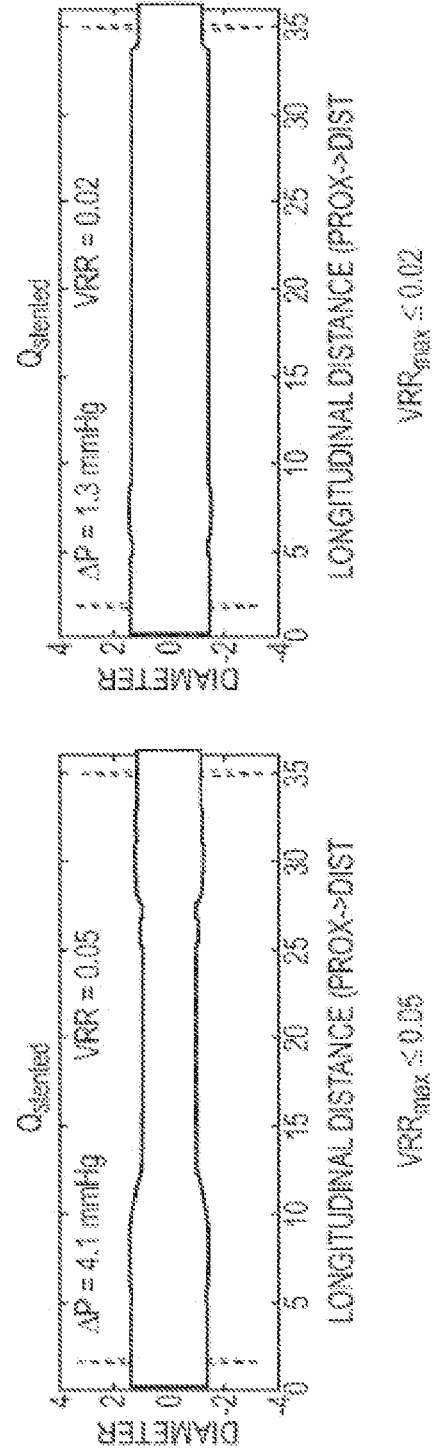
FIG. 26A
FIG. 26B

LUMEN MORPHOLOGY AND VASCULAR RESISTANCE MEASUREMENTS DATA COLLECTION SYSTEMS APPARATUS AND METHODS

RELATED APPLICATIONS

This application is a continuation of U.S. patent application Ser. No. 16/549,814, filed on Aug. 23, 2019, which is continuation of U.S. patent application Ser. No. 13/796,710 filed on Mar. 12, 2013, which is a continuation of U.S. application Ser. No. 12/888,347, filed on Sep. 22, 2010 (now U.S. Pat. No. 9,138,147), which claims priority to and the benefit of U.S. Provisional Application No. 61/244,992, filed on Sep. 23, 2009, and U.S. Provisional Application No. 61/334,834, filed on May 14, 2010, the disclosures of which are incorporated herein by reference.

FIELD OF INVENTION

This invention relates generally to the field of optical coherence tomographic imaging and more specifically to optical coherence techniques for diagnosing and treating vascular stenoses.

BACKGROUND OF THE INVENTION

Coronary artery disease is one of the leading causes of death worldwide. The ability to better diagnose, monitor, and treat coronary artery diseases can be of life saving importance. Intravascular optical coherence tomography (OCT) is a catheter-based imaging modality that employs safe, non-ionizing near-infrared light to peer into coronary artery walls and present images valuable for the study of the vascular wall architecture. Utilizing broad-band coherent light, interferometry, and micro-optics, OCT can provide video-rate in-vivo tomography within a diseased vessel with resolution down to the micrometer level. This level of detail enables OCT to diagnose as well as monitor the progression of coronary artery disease.

The quantitative assessment of vascular pathology and its progression involves the calculation of different quantitative measures such as the vessel cross-sectional area, mean diameter, and blood flow resistance, all of which rely on the accurate identification of the luminal border. While the luminal border in OCT images is clearly identifiable by the human eye, it is tedious, expensive, and time consuming to manually trace the luminal border. Thus there is a need for a reliable technique that can automatically identify the luminal border.

OCT produces images that are higher in resolution and contrast compared to those of intravascular ultrasound (IVUS). As opposed to IVUS which images through blood, OCT images are typically acquired with blood cleared from the view of the optical probe. This is one reason the luminal border in OCT images is sharper and more defined compared to that in IVUS images.

Cross-sectional diameter and area measurements provide interventional cardiologists with useful guidance for stent sizing and placement. However, the relationship of these geometric measurements to clinically relevant variables, such as ability of the artery to supply an adequate flow of blood to the myocardium when metabolic demands are high, is not well understood. In early studies, the percent stenosis of an individual coronary lesion measured by angiography was found to be a relatively poor predictor of the physiological significance of the lesion. In contrast, several later studies demonstrated that lumen measurements made by quantitative coronary angiography (QCA) and IVUS correlate closely with physiologic measurements of coronary obstruction, including coronary flow reserve (CFR) and fractional flow reserve (FFR). For example, several studies found a high correlation between area stenosis, measured by QCA, and CFR measured by a Doppler flow wire. It appears that the standard angiographic (and IVUS) measures of lesion severity—the minimum lumen area (MLA), percentage stenosis, and lesion length—do indeed convey physiologically relevant information. However, the value of any single geometrical measure as an independent predictor of the physiological significance of a lesion in a wide patient population is not clear.

Several factors contribute to the limitation of standard angiographic and IVUS lumen measurements for assessment of the physiological significance of coronary stenoses. First, the accuracy and reproducibility with which cross-sectional areas can be measured with angiography, which generally has a spatial resolution of 0.2-0.4 mm, are relatively low. The angle of the X-ray projection, in addition to the shadowing effect of lesions with irregular contours, can increase errors significantly beyond the theoretical minimums. Even state-of-the-art IVUS imaging systems, which have resolutions of approximately 0.15 mm in the axial dimension and 0.3 mm in the angular dimension, cannot accurately measure the cross-sectional areas of small eccentric lesions or lesions with irregular borders.

Second, the hemodynamic effects of a lesion depend on local variations of its cross-sectional area integrated over the entire length of a lesion. Therefore, the minimum cross sectional area alone is insufficient to characterize the pressure drop across a lesion at a given flow rate, especially in patients with diffuse coronary disease.

Third, when assessing the physiological significance of a lesion and the potential value of revascularization, it is important to know the relative areas of the reference and stenotic segments, in addition to the absolute value of the minimum lumen area. No single geometrical measure in clinical use today conveys information about both percent stenosis and MLA.

Fourth, the flow resistance or pressure drop caused by an incremental segment of a lesion depends on its shape as well as its cross-sectional area and length. Especially at high blood flow rates, the eccentricity and local slope of the walls of the artery can influence the effective resistance of a lesion, because losses due to flow separation and turbulence depend on local flow velocity.

Finally, in certain patients, the flow reserve of the myocardium supplied by the vessel can be low, due to microvascular disease, flow through collateral branches, or capillary shunts within infarcted myocardium. Therefore, even if the vascular resistance of a lesion in the vessel is high, revascularization may be contraindicated, because the pressure drop across the lesion may be clinically insignificant.

Intravascular OCT imaging, applied in combination with new clinical parameters based on advanced analysis of lesion morphology, has the potential to overcome many of the limitations of conventional measures of lesion severity based on angiography and IVUS. The high resolution of OCT enables accurate measurement of the shape and dimensions of the vessel lumen over the length of the lesion and its adjacent reference segments. Furthermore, advanced models of flow dynamics enable the physiological significance of lesions to be estimated under both normal and hyperemic conditions. It should be realized, however, that the clinical value of quantitative lesion morphology measurements—even when accurate—may be limited by physiological conditions in certain patients. Finally, high-frequency OCT imaging has the advantage that it can precisely delineate three-dimensional contours of long segments of coronary arteries in a few seconds to assist cardiologists in their real-time diagnosis and treatment during PCI procedures.

In spite of advances in intravascular imaging, cardiologists frequently do not take full advantage of the capabilities of OCT and IVUS for planning and evaluating stent deployment, because the measurements currently derived from the images provide insufficient information to predict the effectiveness of treatment. For example, many cardiologists rely on minimum lumen area (MLA) as a key variable in their stenting decisions. If MLA measurements are sufficiently low, the cardiologist may decide to implant a stent. Based on the diameters and locations of reference vessel segments, the cardiologist must then choose the proper position, length, and diameter of the stent. The wrong choice of the size or location of the stent may lead to the failure to restore blood flow and may even cause potentially serious clinical complications, such as stent migration, stent thrombosis, or dissection of the vessel wall. There is a need for new methods for optimization of stent sizing and positioning based on measurements derived from intravascular images. To achieve maximum clinical benefit, these new methods should enable cardiologists to predict the potential physiological consequences of implanting stents of different diameters and lengths in different locations.

The present invention addresses these needs.

SUMMARY OF THE INVENTION

In one aspect, the invention relates to an automated computer-based method of evaluating a region of a lumen. The method comprises the steps of collecting a set of data regarding a vessel segment of length L using an optical coherence tomography system, the set comprising a plurality of cross sectional areas at a plurality of positions along the length; determining a vascular resistance ratio (VRR) using a processor and at least a portion of the set of data; and determining a characteristic of at least a portion of the region disposed along the length L in relation to the vascular resistance ratio.

In one embodiment, the method is applied to the region that contains a stenotic lesion. In another embodiment, the method further comprises the step of displaying at least one numerical or graphical measure of stent length used to treat the stenotic lesion. In yet another embodiment, the step of determining the vascular resistance ratio is performed using a lumped resistor model.

In another aspect, the invention relates to a method for automatically identifying the luminal border in an in-situ OCT vascular image. In one embodiment, the method comprises the steps of generating a mask of the OCT lumen image using a computer; defining a plurality of scan lines in the mask; identifying a region as tissue on each scan line; defining contour segments in response to the plurality of scan lines and the region of tissue on each scan line; identifying valid neighboring contour segments; interpolating missing contour data between valid neighboring contour segments; assessing the likely correctness of the computed contour and indicating to the user on which image frames the computed contour may require manual adjustment.

In one embodiment, the method includes the step of detecting and removing guide wire and similar artifacts. In another embodiment, the identification of a tissue region includes the steps of finding a plurality of start/stop pairs on each scan line; calculating thickness and gap of each said start/stop pair; calculating a weight based on said thickness and said gap; and defining the tissue region based on the largest weight of tissue and gap. In another embodiment, the step of defining connected contour includes finding the scan line with the largest weight; searching for discontinuities in both directions from the scan line to define a valid segment; and identifying the root of the contour as the longest of the valid segments. In still yet another embodiment, the step of identifying valid neighboring contour includes finding the nearest clockwise and counter-clockwise neighbors of each of the contour segments that pass angular, radial, and Euclidean distance thresholds.

In another embodiment, the step of detection and removal of guide wire shadow artifact comprises the steps of clearing an image binary mask by fitting an ellipse to the foreground data of the mask and blanking the area inside ellipse; building an intensity profile using the cleared mask; identifying the guide wire shadow region in the intensity profile; detecting a guide wire offset within the shadow region; collecting the midpoint of detected guide wires on all frames; building a minimum spanning tree using the collected midpoints; and pruning the resulting minimum spanning tree to remove outliers resulting from non-guide wire shadows. In another embodiment, the step of interpolating missing data includes the steps of identifying required interpolation control points with valid contour data on both ends of the missing contour segment; and using the control points to interpolate the missing contour segment. In still yet another embodiment, the steps are performed on all missing contour segments that need to be interpolated. In yet another embodiment, the step of searching for discontinuities comprises the steps of calculating a scan line-to-scan line offset change histogram; smoothing said histogram; identifying the smallest change with zero count from the histogram; and using the smallest change as a continuity measure.

In another embodiment, the step of evaluating the correctness of the computed contour comprises the steps of computing an "Error Measure" by fitting an ellipse to the computed contour; computing the root mean square error between the computed contour and the fitted ellipse; normalizing the root mean square error to the average diameter of the ellipse; and multiplying the normalized root mean square error by the ratio of the number of scan lines where the lumen was successfully detected to the total number of scan lines in the image frame. In another embodiment, the resulting Error Measure parameter is compared to a threshold and, for image frames where the threshold is exceeded, the user is notified that manual contour correction may be required. In yet another embodiment, the notification can take the form of "alert frames" drawn on a longitudinal display of the images of the pullback region.

In another aspect, the invention relates to an automated method for quantifying a vascular resistance including the steps of selecting proximal and distal frames of an OCT image; calculating actual vascular resistance of the vascular segment enclosed by said proximal and the distal frames; calculating a total vascular resistance of the vascular segment; and calculating vascular resistance ratio using the actual vascular resistance and said total vascular resistance. In one embodiment, the step of calculating actual vascular resistance comprises the steps of extracting luminal contours of all frames enclosed by the proximal and the distal frames inclusive; calculating cross-sectional areas from the extracted contours; constructing a smooth area graph; and using the smooth area graph in the actual vascular resistance calculation. In another embodiment, the step of calculating the total vascular resistance comprises the steps of: fitting a shape between said proximal and said distal frames; and calculating cross-sectional areas of the shape at all frame positions enclosed by the proximal and the distal frames inclusive. In yet another embodiment, the step of constructing a smooth area graph includes the steps of constructing a graph using the cross-sectional areas; interpolating missing area values on the graph; and smoothing the resulting graph. In still yet another embodiment, vascular resistance is calculated by computational fluid dynamics from the detected three-dimensional luminal border between the proximal and distal planes.

Another aspect of the invention is a method of placing a stent including the steps of: (a) measuring the parameters in the region of interest in an OCT image of a vessel; (b) simulating the placement of the stent in the region of interest; (c) recalculating the parameters in the region of interest; and repeating Steps b and c until the desired result is obtained.

BRIEF DESCRIPTION OF DRAWINGS

The invention is pointed out with particularity in the appended claims. The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

FIGS. 7a and b are samples of an OCT image and its resulting median mask, respectively, according to an illustrative embodiment of the invention;

FIG. 8 is a diagram of a scan line with multiple start/stop pairs according to an illustrative embodiment of the invention;

FIGS. 25a and 25b are examples showing the pre- and (predicted) post-stented mean-diameter lumen profiles, respectively, resulting from optimization according to one embodiment of the invention; and FIGS. 26a and 26b are examples showing the pre- and (predicted) post-stented mean-diameter lumen profiles, respectively, resulting from optimization according to another embodiment of the invention.

DETAILED DESCRIPTION OF THE INVENTION

Figure 1A:
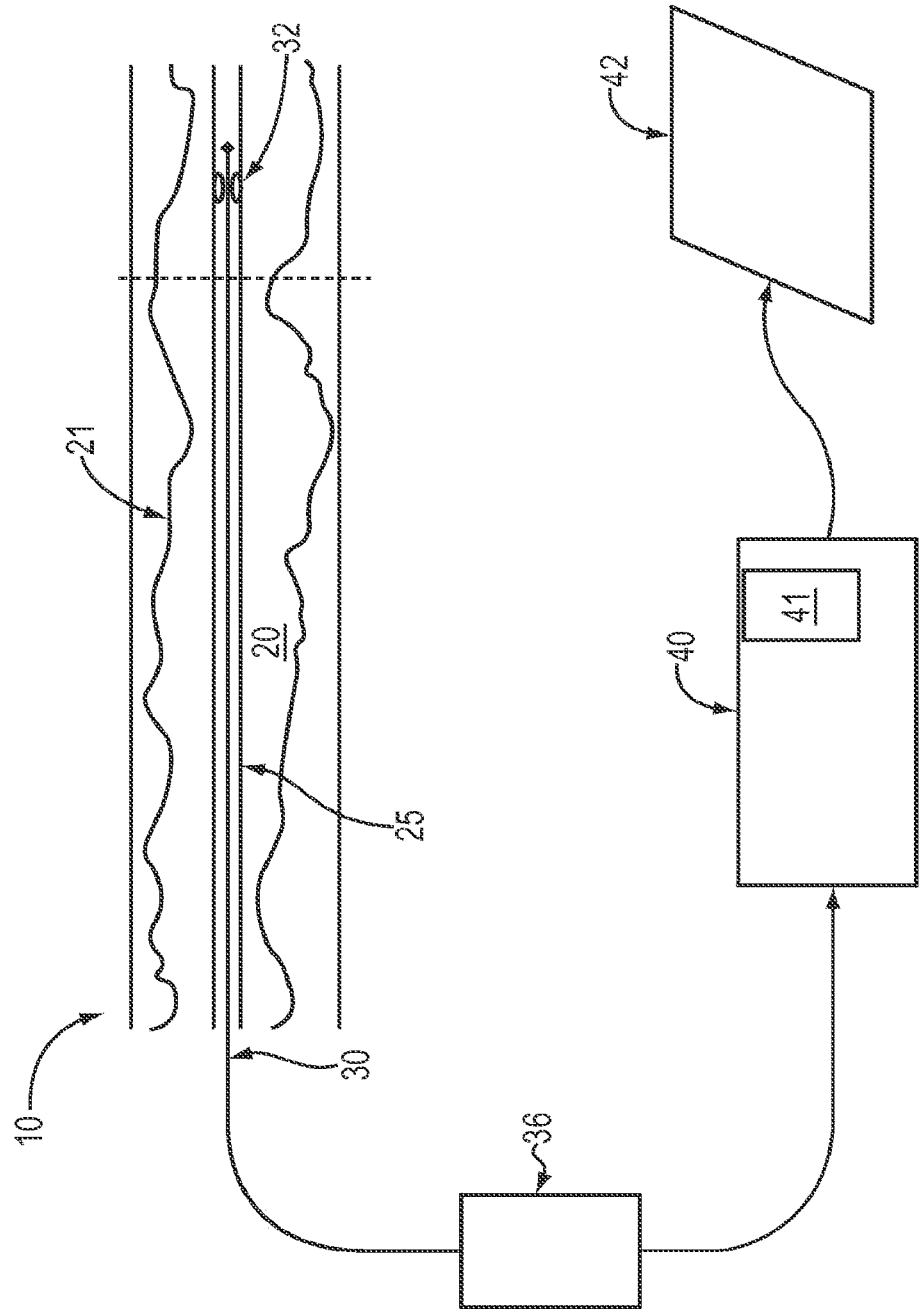
FIG. 1A is a generalized schematic of an OCT data collection system having an imaging probe disposed in a vessel of interest.

FIG. 1a is a high level schematic diagram depicting components of an OCT system 10 constructed in accordance with the invention. FIG. 1a is highly generalized and not to scale. A vessel of interest 20 defining a lumen having a wall 21 is imaged using catheter 25 having a catheter portion having an optical fiber-based imaging probe 30 disposed therein. The catheter 25 includes a flushing subsystem having flush ports 32. The flushing system can be of any suitable type or variety that displaces a sufficient amount of blood such that in vivo OCT data collection can proceed using the probe 30. The system 10 includes an OCT system or subsystem 36 that connects to the imaging probe 30 via an optical fiber. The OCT system or subsystem 36 can include a light source such as a laser, an interferometer, various optical paths, a clock generator, photodiodes, and other OCT system components.

In one embodiment a computer or processor is part of the OCT system 36 or is included as a separate subsystem 40 in electrical communication with the OCT system 36. The computer or processor 40 includes memory, storage, buses and other components suitable for processing data. for lumen detection and pull back data collection as discussed below. In one embodiment, the computer or processor includes software implementations or programs 41 of the methods described herein that are stored in memory and execute using a processor. A display 42 is part of the overall system 10 for showing cross-sectional scan data as longitudinal scans or in other suitable formats.

In brief overview, the present invention provides a method and apparatus of automatically locating a lumen boundary at a position in a vessel of interest (using an OCT image or the underlying data) and from that measuring the diameter of the vessel. From the diameter of the vessel and calculated blood flow rate a number of clinically significant physiological parameters are then determined and various images of interest generated. One use of these images and parameters is to aid the clinician in the placement of a stent. The system, in one embodiment, uses these measurements to allow the clinician to simulate the placement of a stent and determine the effect of the placement. In addition, from these patient parameters various patient treatments are then performed.

Figure 1B:
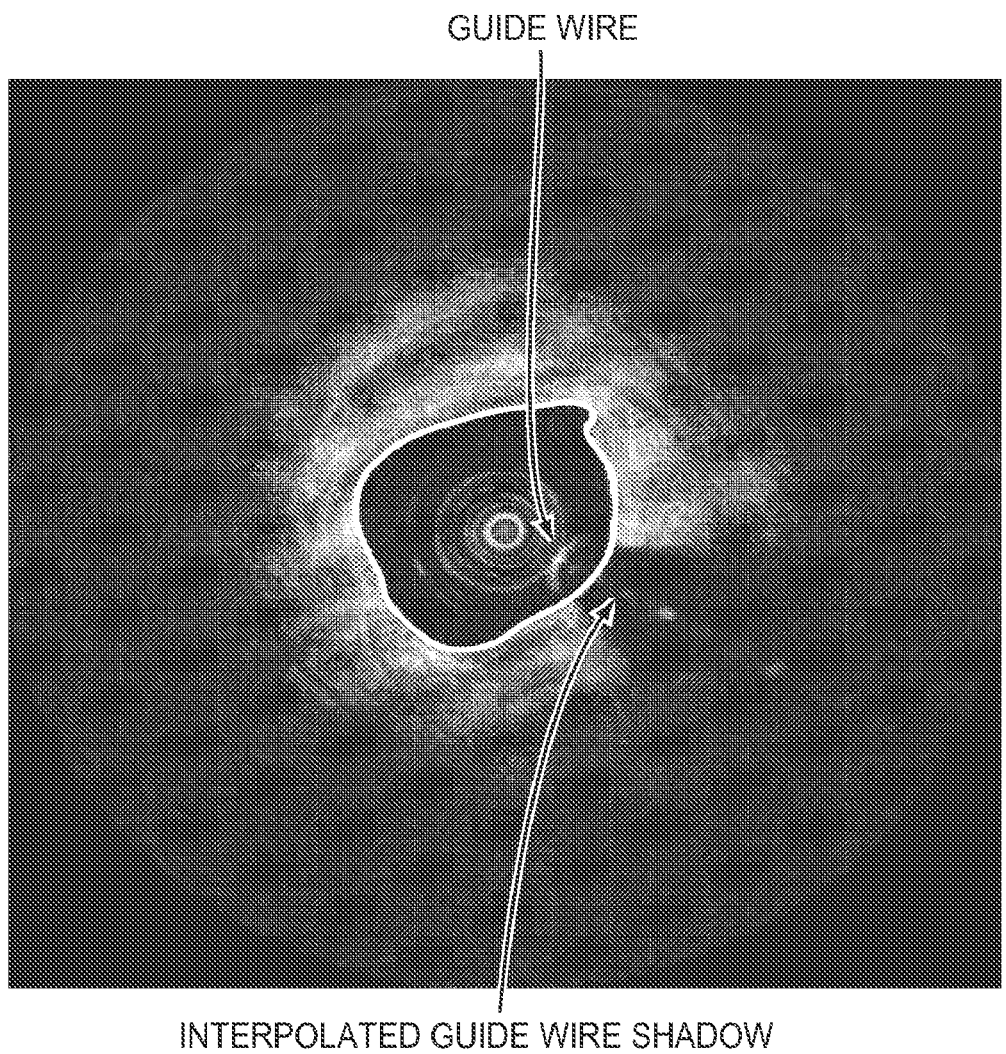
FIG. 1B is an example of a sample detected contour interpolated according to an illustrative embodiment of the invention.
Figure 2:
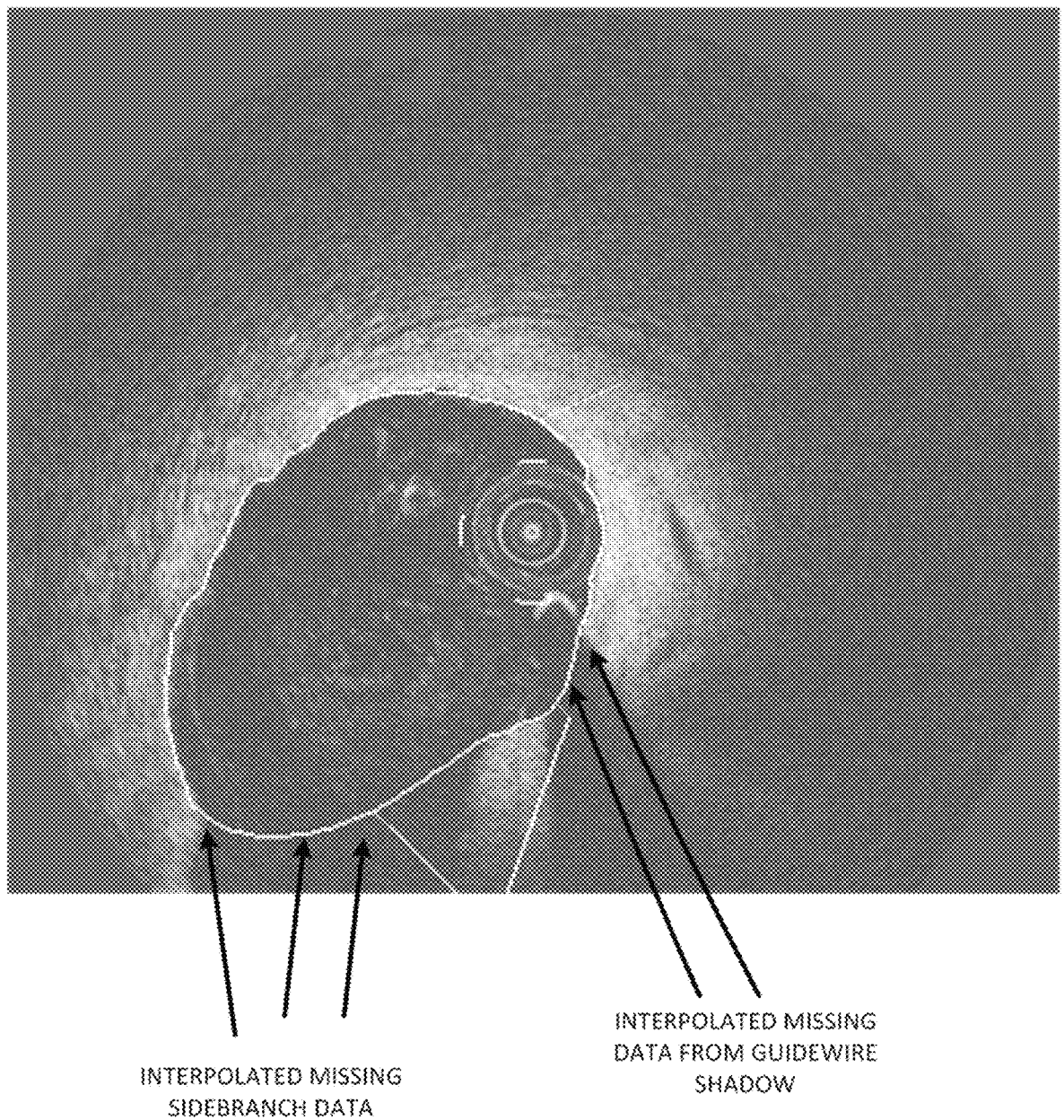
FIG. 2 is an example of a sample detected contour with guide wire and side branch missing data interpolated according to an illustrative embodiment of the invention.
Figure 3:
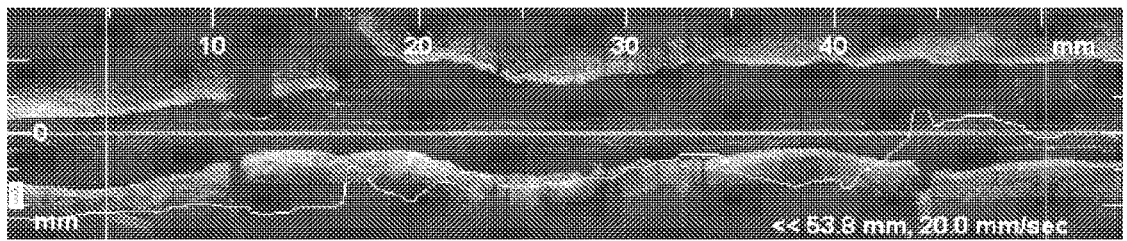
FIG. 3 is an example of a sample area graph after smoothing according to an illustrative embodiment of the invention.
Figure 4:
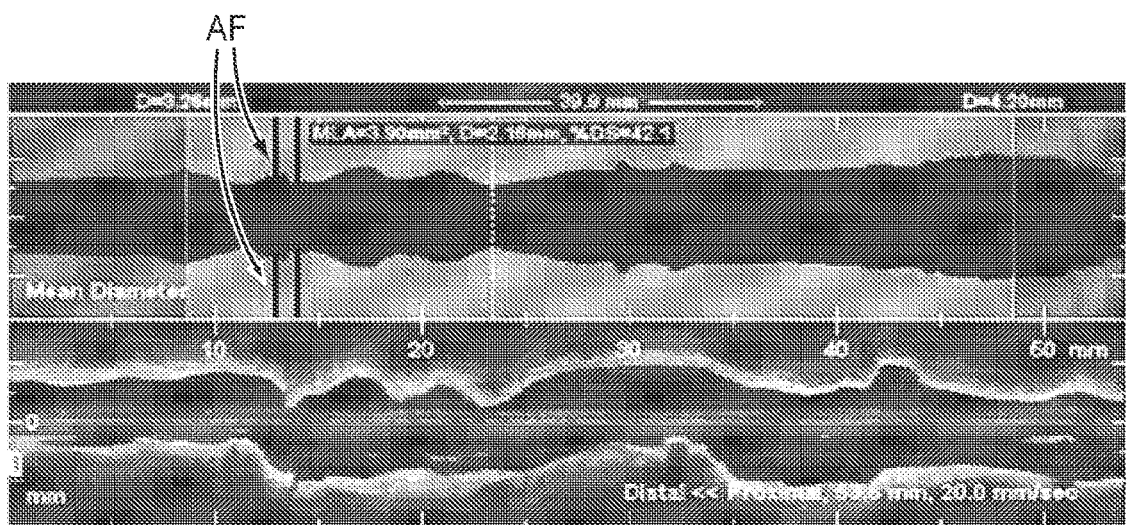
FIG. 4 is an example of an alternative display in which the mean cross-sectional diameters and "Alert Frame" feedback are shown in a separate panel above the OCT L-mode image according to an illustrative embodiment of the invention.

As a first step, the system determines the lumen boundary. Generally, data taken by an OCT system is used with the methods described herein to recognize and avoid residual blood, guide wire reflections, and other structures that may appear to be part of the vessel wall. Interpolation of a continuous boundary is accomplished by imposing continuity of the inner surface of the vessel across neighboring frames. FIGS. 1 and 2 show examples of lumen contours drawn automatically by the software based method on two frames of a frequency domain OCT (FD-OCT) image sequence. To help the user identify stenotic and normal vessel segments, in one embodiment the software shows the cross-sectional areas calculated automatically for all frames in a sequence as a graph superimposed on the longitudinal (L)-mode image (FIG. 3). The lines 10, 10' indicate the position of the user-selected proximal and distal reference frames. An alternative embodiment of the display shows the mean diameter values profile in a separate panel above the L-mode display (FIG. 3). FIG. 4 shows an alternative display in which the mean cross-sectional diameters and an "Alert Frame" feedback are shown in a separate panel above the OCT L-mode. The alert frame, labeled AF indicates a frame where the system believes human intervention is required to verify the values shown.

The mean diameter of each cross-section is calculated either as the diameter of a circle with an area equal to that of the cross section or as the mean of the chord lengths at all angles drawn through the centroid of the lumen cross-section. In one embodiment, the minimum lumen area (MLA), proximal and distal reference areas, percent diameter stenosis, and the length between references are displayed numerically in the same panel.

Figure 5:
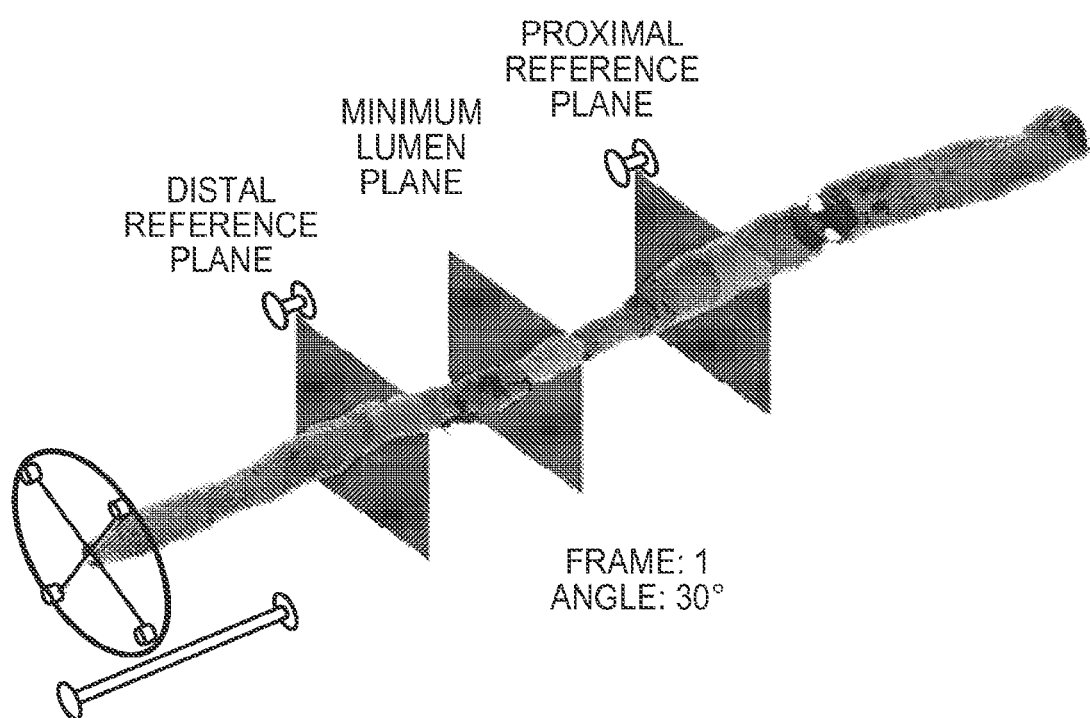
FIG. 5 is an example of a 3D display of the shape of the lumen of a vessel reconstructed from an OCT image in which lumen contours were traced automatically according to an illustrative embodiment of the invention.

In one embodiment, the system then also generates a three-dimensional rendering of the shape of the vessel lumen as calculated from the cross-sectional measurements. An example is shown in FIG. 5. The user sets the positions of the proximal and distal reference planes manually on the 3D image by dragging either line marker in the L-mode display or reference planes on the 3D display. The longitudinal position between the reference markers at which the cross-sectional area is smallest is found automatically and a separate marker plane is placed automatically by the computer at this position. In one embodiment, the entire display can be rotated around the longitudinal axis by steering a compass wheel in the display.

Figure 6A:
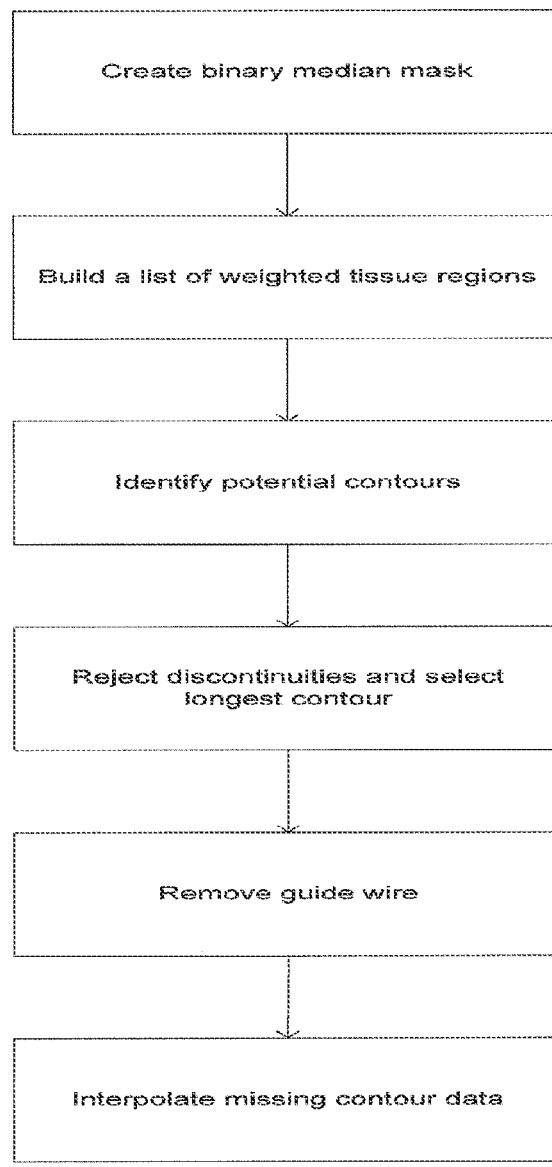
FIG. 6a is a flow chart of an embodiment of the method to detect the shape of the lumen of the vessel OCT image according to an illustrative embodiment of the invention.

Referring to FIG. 6a, the method of detecting the lumen of a vessel in an OCT image is briefly described. First an image mask is created. In one embodiment, the image mask is a binary image mask to demark the general contour of the lumen wall. Next, a list of weighted tissue regions is created and potential contours defined. Discontinuities in these contours are rejected and the longest remaining contour selected. Any artifacts such as the shadow of the guidewire are removed and missing contour data is interpolated to correct for missing portions of the image.

Figure 6B:
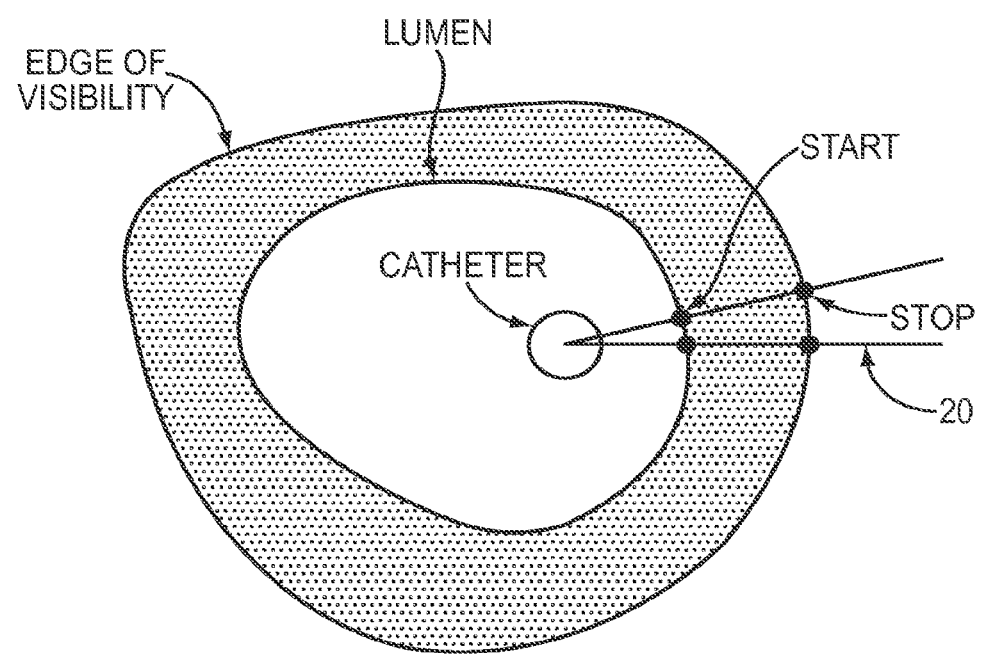
FIG. 6b is a diagram of start/stop pairs on scan lines according to an illustrative embodiment of the invention.

In more detail and referring to FIG. 6b, the smallest data unit in an OCT image is called a sample. A sequence of samples along a ray 20 originating at the catheter center to the maximum imaging depth is called a scan line. An OCT image is typically acquired one scan line at a time. A cross-sectional image is formed by a collection of scan lines as the OCT catheter rotates. Further, to image a segment of the vessel, the catheter is moved longitudinally along the vessel while rotating, hence acquiring a set of cross-sectional images in a spiral pattern. It should be noted that while the present invention is described in the context of OCT images, the present invention is not so limited. Thus, for example, identifying any border, boundary, or contour in any vascular image is within the spirit and scope of the present invention.

A cross-sectional image of the vessel is created for each complete rotation of the optical probe. These images are individually preprocessed and a suitable threshold is applied to create a binary foreground/background image mask, wherein the foreground is defined to contain the potentially relevant image information (e.g. the vessel wall) and the background represents the empty luminal space between the catheter and vessel wall, as well as the 'noise floor' beyond the deepest imaging depth within the wall. The image mask is further processed by convolving the image mask with a median filter that has a suitable width W and a suitable height H. This operation fills in the gaps and removes the noise as each of the image mask values is replaced by the median value in its W×H neighborhood window. An example of a resulting mask is shown in FIG. 7b. The resulting mask has the same dimensions as the original cross-sectional image.

In still more detail, in one embodiment of the invention, each scan line of the mask is processed to find all pairs of start and stop samples as shown in FIG. 6b. The start sample denotes the start of a tissue (foreground) region while the stop sample represents the end of a tissue region. The thickness of a tissue region is calculated as the number of samples between a start sample and a stop sample (i.e. the number of samples identified as foreground). A gap region is calculated as the number of samples between a stop sample and a start sample (i.e. the number of samples identified as background).

In any one scan line it is possible to have more than one region identified as tissue, as shown in FIG. 8. This is mainly due to (but not limited to) blood artifacts, if the lumen is not completely cleared of flowing blood during the image acquisition. To avoid artifacts and select the pair that best represents the tissue region in a given scan line, a weight is associated with each detected region. The weight, in one embodiment, is calculated as:

$$\text{Weight} = (\text{gap} * \text{thickness}^2) \quad (1)$$

so as to favor the thickest isolated region, as blood artifacts are thinner than the imaged vessel wall. It should be appreciated that this invention is not limited to this particular weight calculation.

At this point in the procedure, every scan line in a given cross-sectional image should have, at most, one sample that will be on the lumen contour. The calculated weight associated with the sample on any given scan line is kept for further utilization. Some scan lines such as those in a side branch of a vessel might not have detected samples corresponding to a contour.

Figure 9:
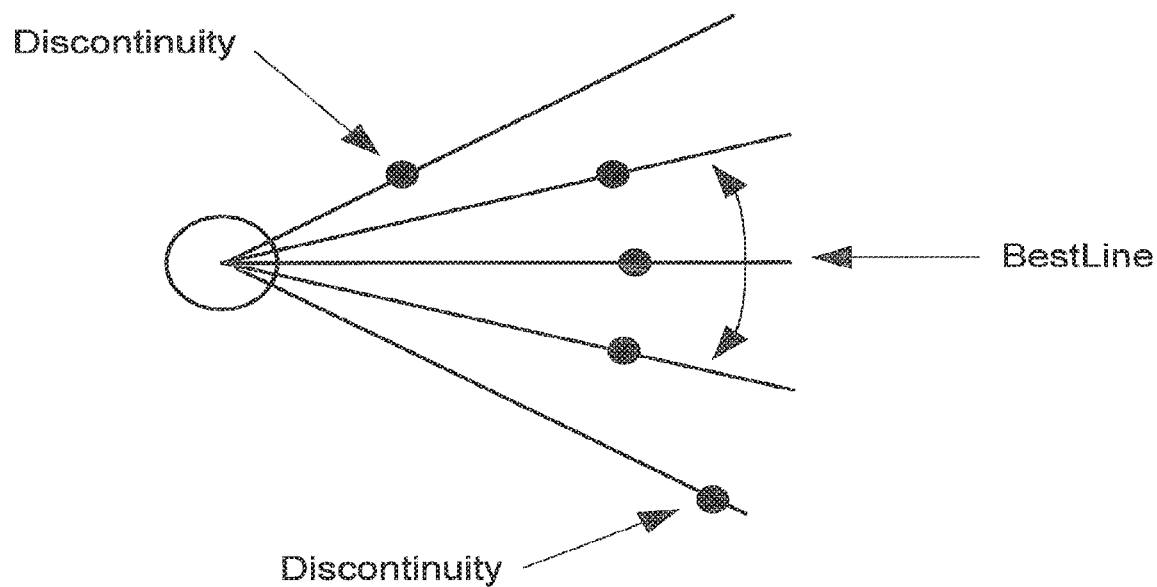
FIG. 9 is a diagram of a discontinuity search according to an illustrative embodiment of the invention.

A contour segment can be defined, in one embodiment, as a group of contiguous scan lines with no discontinuities. A discontinuity is a scan line-to-scan line change in the sample number (offset) that exceeds a predetermined continuity threshold. To identify all possible contour segments, the method begins by searching for the line with the largest weight among the lines not yet grouped in segments (initially, these are all scan lines in a given cross-sectional image). A segment is identified by searching for discontinuities clockwise and counter-clockwise from the line with the largest weight as illustrated in FIG. 9. One way to determine a discontinuity threshold is to compute and smooth a line-to-line change in an offset histogram.

Figure 10:
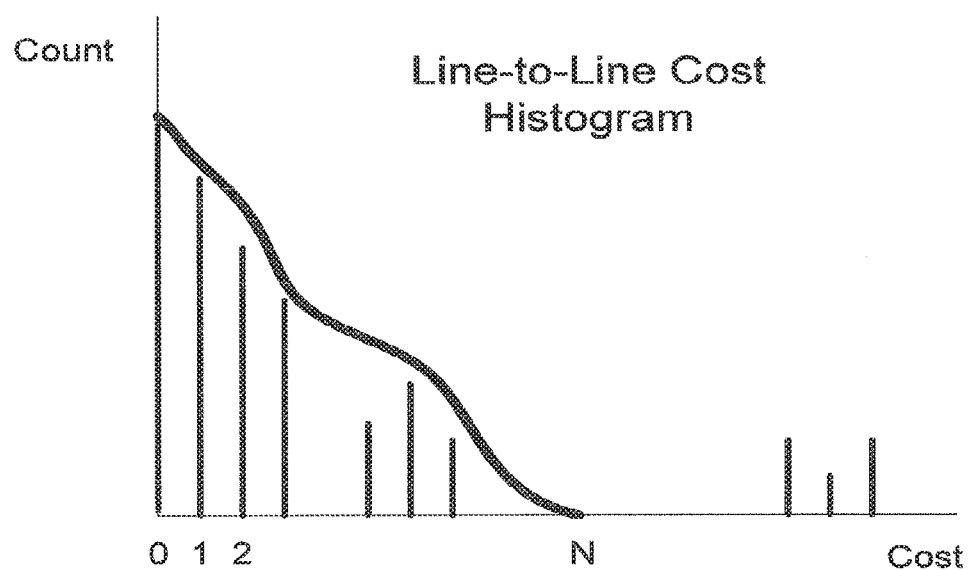
FIG. 10 is a histogram depicting a line-to-line change according to an illustrative embodiment of the invention.

FIG. 10 shows an illustration of a possible smoothed histogram. The cost represents the line-to-line change of offset, and the count represents the frequency (the number of occurrences) for a given change of offset. Such a histogram typically has a bi-modal distribution. The peaks with the lower costs represent acceptable, physiologically feasible changes in offsets, while the peaks with the higher costs represent transitions to and from artifacts. In FIG. 10, a region of zero count separates the two peaks of the bi-modal histogram. The smallest cost with zero count is identified and used as a threshold. It should be noted that this invention is not limited to this one particular method for determining the discontinuity threshold.

The luminal contour is a possible grouping of one or more contour segments. The root (first segment to add to the contour) of the contour is selected as the longest valid segment. The nearest clockwise and counter-clockwise neighboring segments of each potential contour segment are identified. Valid neighbors must pass an angular distance threshold, a radial distance threshold, and a Euclidian (direct connection) distance threshold. Each potential contour is then traversed clockwise and counter-clockwise and the longest contour is selected.

Figure 11A:
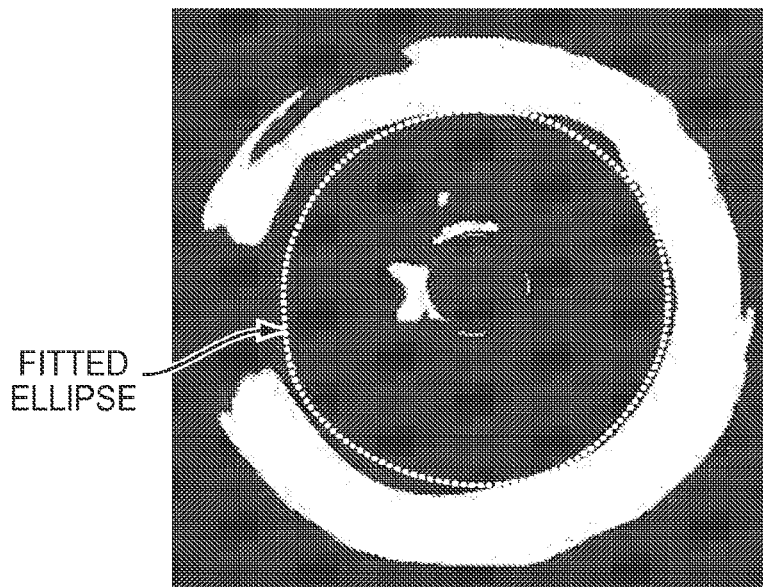
FIG. 11a is a sample of a median mask before clearing according to an illustrative embodiment of the invention.
Figure 11B:
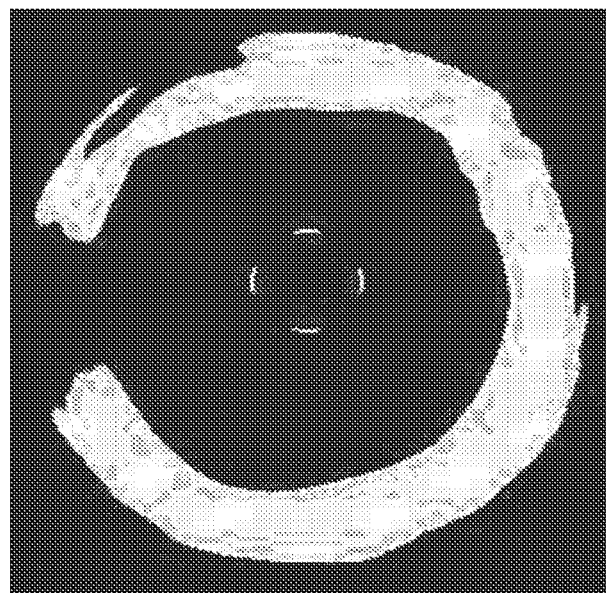
FIG. 11b is a sample image of a median mask after clearing according to an illustrative embodiment of the invention.
Figure 11C:
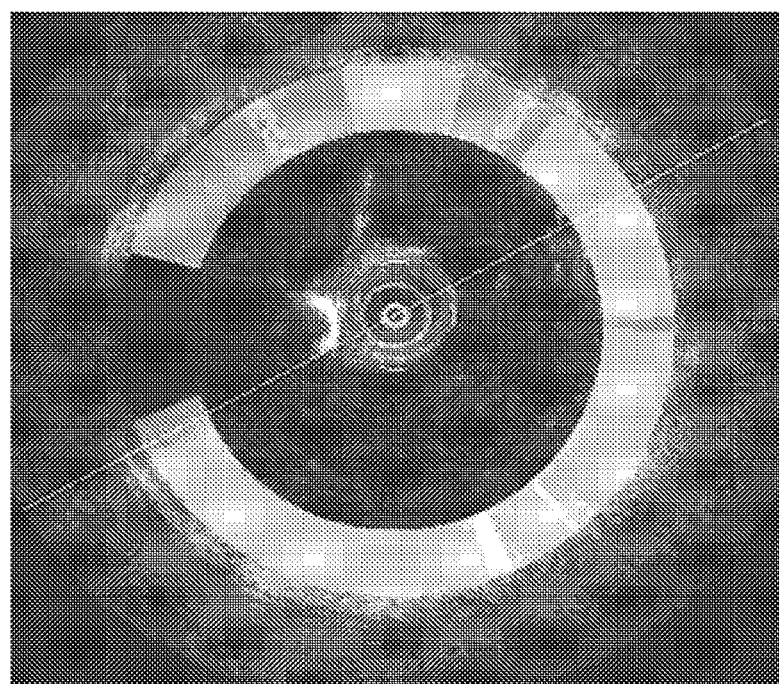
FIG. 11c is a sample image of intensity profile according to an illustrative embodiment of the invention.
Figure 11D:
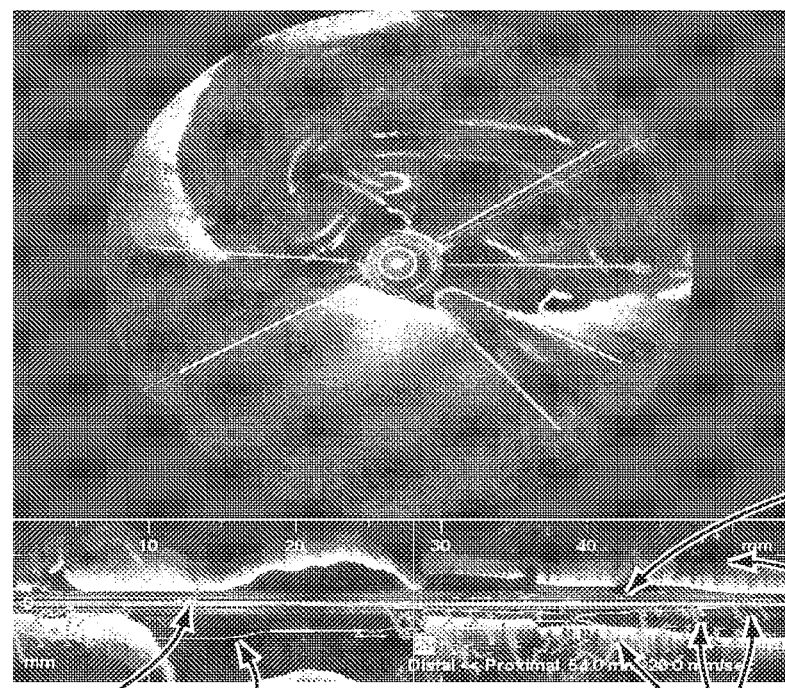
FIG. 11d is a sample image of a minimum spanning tree before pruning according to an illustrative embodiment of the invention.
Figure 11E:
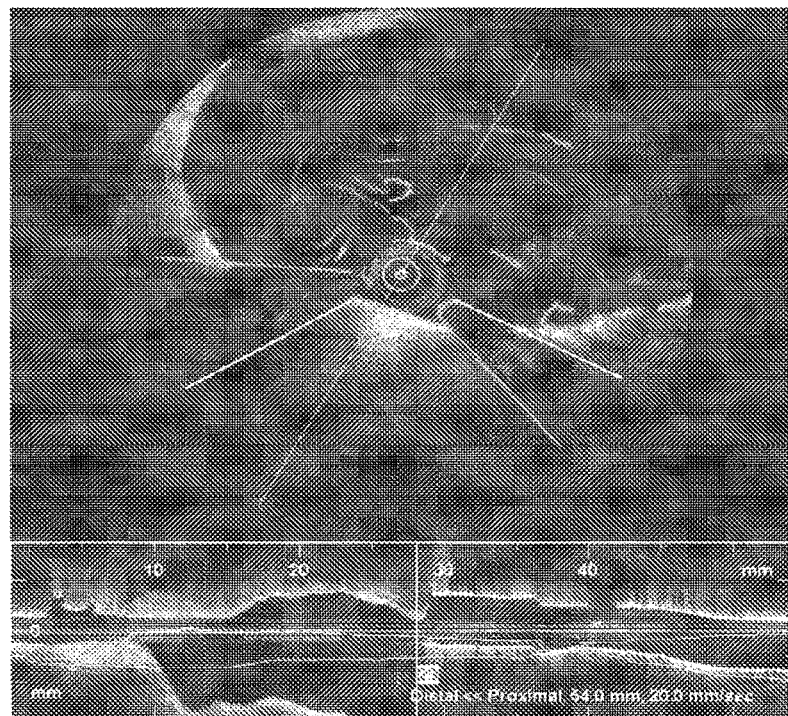
FIG. 11e is a sample image of a minimum spanning tree after pruning according to an illustrative embodiment of the invention.

To detect and remove the guide wire and other similar artifacts from the image, an ellipse is fitted to the foreground of a median mask (shown in FIG. 11a). The area inside of the ellipse is then blanked to remove any small disconnected regions as shown in FIG. 11b. Applying the resulting mask to the OCT image, the average intensity value along each scan line of the masked OCT image is calculated (shown in FIG. 11c as a plurality of scan lines of varying shading). The guide wire shadow is then identified via the use of a suitable gradient filter, such as the Sobel edge detector and the guide wire offset (its radial distance from the catheter) is detected inside the guide wire shadow region. Shadows from other sources such as stent struts and residual blood are also detected and need to be delineated from the guide wire shadow. The midpoints of all detected shadow regions on all frames is then collected and used as nodes to build a minimum spanning tree. In one embodiment of the invention, the nodes of the tree are selected and connected such that: no points on the same frame are connected together; and any given node is connected to a parent node that minimizes a weight value. In one embodiment the weight value is calculated as the sum of the distance and slope difference between a node and its parent node. A sample resulting tree is shown on the L-mode display in FIG. 11d. Finally, the tree is pruned by removing small branches (according to a suitable threshold) as shown in FIG. 11e.

Missing contour data is interpolated as shown in FIGS. 1 and 2. In one embodiment, a smooth curve between two points is interpolated using the cosine function. The range of values of a cosine function is +1 to −1 inclusive in the domain 0 to $\pi$. Since the interpolation between two points requires a weighting range from 0 to 1 inclusive, it is desirable to adjust the cosine range. Using the function (1−cos) provides a range from 0 to 2 inclusive and dividing by 2 yields (1−cos)/2 with the required range from 0 to 1.

Alternatively, one can use any suitable function such as the cubic function or the Hermite function to interpolate missing data using four or more control points instead of two. Interpolating a point between two points $y_1 = f(x_1)$ and $y_2 = f(x_1 + \Delta x)$, calculates the value of the point on a preselected curve between $x_1$ and $x_2$. The general relation is given by $(1-\alpha)y_1 + (\alpha)y_2$, where a is the interpolation weight ranging from 0 at $x_1$ to 1 at $x_1 + \Delta x$. Using the previously described cosine weighting method, the weight of a point at given distance d from $x_1$ is calculated by $\alpha = (1 - \cos(\pi * d / \Delta x))/2$. It should be noted that this invention is not limited to any one particular interpolation method.

Figure 12:
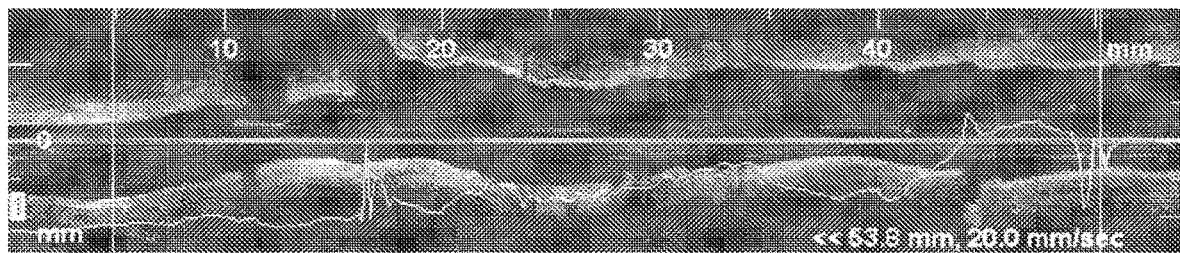
FIG. 12 is an example of a sample area graph without smoothing according to an illustrative embodiment of the invention.

For an entire longitudinal segment of interest for a vessel, an area graph vs. longitudinal position is constructed from the individually calculated cross-sectional areas as shown in FIG. 12. For any missing data (where the contour extraction might have failed for any reason) a suitable interpolation method can be used. The resulting graph (FIG. 3) is smoothed to remove sharp transitions in the area graph. One way to smooth the area graph is to use a median filter. It should be noted that this invention is not limited by any one particular smoothing method.

Once the cross-sectional area of the vessel has been determined the severity of any stenotic region is then characterized. One measure of severity of a stenotic lesion imaged by OCT is provided by a parameter called the vascular resistance ratio (VRR). The VRR quantifies the blood flow resistance of a stenotic vessel segment relative to the flow resistance of the entire vessel branch, assuming maximum vasodilation of the peripheral coronary vasculature. The VRR is defined as:

$$VRR \equiv \frac{R_s}{R_T} \quad (2)$$

where $R_s$ is the blood flow resistance of the stenotic segment and $R_T$ is the total flow resistance of the branch vessel in which the stenotic region is located. VRR ranges from 0 (no vessel narrowing) to 1 (all flow resistance due to the stenosis).

The calculation of VRR is based on a lumped parameter model (FIG. 13) of the blood flow through a stenosed branch of a coronary artery under hyperemic conditions. In this model, the blood flow $Q$, driven by the difference between the arterial blood pressure $P_a$ and the coronary venous pressure $P_v$, is limited by the total flow resistance ($R_T$) of the branch of the vessel through which the blood is flowing. $R_T$ is composed of the sum of three resistance elements, $$R_T = R_s + R_e + R_{mv} \quad (3)$$

where $R_s$ is the blood flow resistance of the stenotic segment, $R_e$ is the blood flow resistance of the remaining epicardial length of the branch, and $R_{mv}$ is the microvascular resistance of the peripheral coronary vascular bed.

In general, the values of all three resistance elements depend on blood flow, but only $R_s$ is shown explicitly as a function of $Q$, because $R_{mv}$ and $R_e$ are only weakly flow-dependent under conditions of maximum vasodilation. During drug-induced hyperemia, $R_{mv}$ is approximately constant and is given by:

$$R_{mv} = \frac{P_a - P_v}{Q_{max}} \quad (4)$$

where $Q_{max}$ is the maximum blood flow that can be achieved in the branch when the pressure drop across the epicardial arteries is negligible (i.e., $R_s + R_e \to 0$). $Q_{max}$ equals the product of the mean hyperemic Doppler blood velocity, $v_{max}$, measured in a normal reference segment of the artery and the cross-sectional area, $A_n$, of the artery measured in the same location, $Q_{max} = v_{max} A_n$. Velocity may also be measured using speckle caused by particulates in the stream and detected in the OCT image. Based on these relationships, Eqn. 4 can be re-formulated in terms of hyperemic velocity:

$$R_{mv} = \left(\frac{P_a - P_v}{v_{max}}\right) \cdot \frac{1}{A_n} \quad (5)$$

The quantity in braces, which has units of mm Hg cm$^{-1}$s, is the hyperemic microvascular resistance index, designated as h-MRv. An important advantage of determining hyperemic resistance using velocity instead of flow is that velocity normalizes flow for differences in arterial diameter due to branching and is preserved between proximal and distal segments. Table 1 lists published values of h-MRv measured during PCI with a Doppler flow wire. The values lie within a relatively narrow range for both treated and untreated vessels.

In the calculations shown it is assumed that h-MRv is a constant approximately equal to 1.0 mm Hg cm$^{-1}$s, a value that lies at the lower end of the distribution of resistances in Table 1 for upsized stented arteries. The value of $A_n$ in Eq. 5 is assumed to equal the cross-sectional area of the proximal segment of the reference vessel. For a 3-mm diameter artery, Eqn. 5 yields $R_{mv}$=17 mm Hg cm$^{-3}$s with a corresponding maximum flow of about 4.7 ml/s at an arteriovenous pressure difference of 80 mmHg.

The second component of the total resistance in Eqn. 3, $R_e$, the epicardial resistance outside of the stenotic segment of the vessel, is usually small compared to $R_s$ and $R_{mv}$. Its value can be estimated by integrating the flow resistance along the length of the vessel, $L_e = L_T - L_s$, where $L_T$ is the total length of the coronary branch and $L_s$ is the length of the stenotic segment imaged by OCT. Assuming that no significant flow-limiting stenoses are present outside of the stenotic segment and that the mean cross-sectional area of the vessel remains the same as in the mean cross-sectional area, $\overline{A}^n$, of the reference segments adjacent to the stenosis imaged by OCT, $R_e$ can be calculated using Poiseuille's law, as $$R_e = \frac{8\pi \eta L_e}{\overline{A}_n^2}, \quad (7)$$

where $\eta$ is the viscosity of the blood and the mean area is given by $$\overline{A}_n = \frac{1}{M}\sum_{i=1}^{M} A_i \quad (8)$$

In this equation, the cross-sectional lumen areas $A_i$ are measured in the frames of the OCT image located outside of the stenotic region, so that the total number of available frames M depends on the lengths of the proximal and distal reference segments in the image. Although the total lengths of the epicardial coronary branches are not, in general, the same, it is assumed that $L_T$=8 cm for the main coronary arteries (LAD, LCX, and RCA), so that $L_e$ can be found directly by subtracting the length of the OCT image region from $L_T$. A better estimate of the epicardial length can be obtained from lengths measured by angiography, if such data is available. The mean area is estimated as the average of the diameters of the proximal and distal reference segments.

Calculation of the stenotic resistance, $R_s$, in Eqn. 3 is complicated by its dependence on blood flow. $R_s$ composed of a flow-independent component that results from viscous losses and a flow-dependent component that results from kinetic losses. A variety of methods have been developed for calculation of the flow resistance of stenotic lesions. Three different embodiments of methods (one analytical and two numerical) by which $R_s$ can be calculated based on measurements of lumen morphology by OCT will now be discussed.

Figure 14:
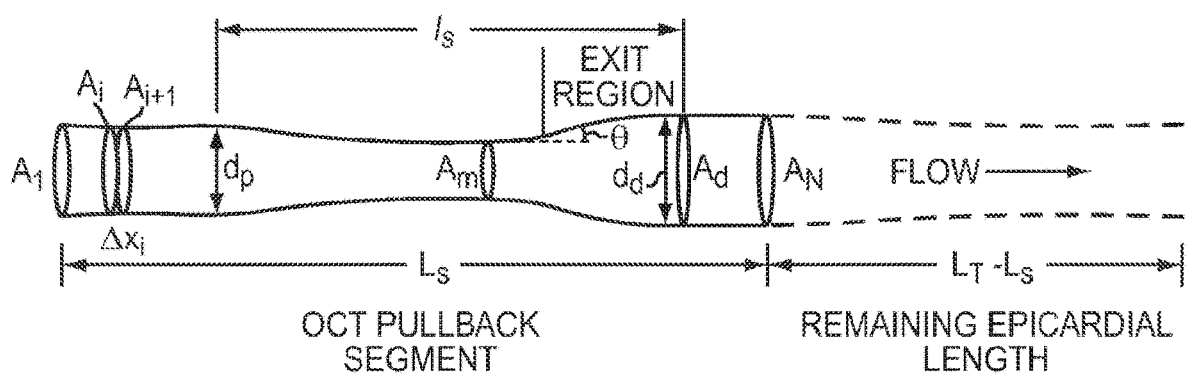
FIG. 14 is an exemplary model geometry for calculation of VRR according to an embodiment of the invention.

The first embodiment of a method for calculation of $R_s$ is adapted from a model of pressure loss in stenotic lesions developed by Kirkeeide. FIG. 14 illustrates the cylindrically symmetrical geometry on which the model is based. The total resistance of the stenosis is assumed to consist of two flow-independent components and a flow-dependent component:

$$R_s = R_p + R_v + k_e Q \tag{9}$$

Here $R_p$ represents losses due to viscous wall friction, calculated according to Poiseuille's law as:

$$R_p = 8\pi\eta C_1 \left[ \sum_{i=1}^{N} \frac{\Delta x_i}{A_i^2} - \sum_{(Exit\ regions)} \frac{\Delta x_i}{A_i^2} \right] \tag{10}$$

This resistance equals the total integrated viscous losses along the vessel minus the losses in the exit regions where flow separation occurs. Exit regions are defined as the segments of the artery within which the exit angle ($\theta$ in FIG. 14) exceeds a threshold value (typically 5°). In these equations $C_1 = 0.86$, based on results of experiments conducted by Kirkeeide.

The second flow-independent component of $R_s$ in Eq. 9, which represents the additional viscous losses that occur at the entrance of regions of sudden narrowing of the vessel wall, is given by:

$$R_v = 8\pi\eta C_2 \left[ \frac{d_p}{A_m^2} \right] \tag{11}$$

where $d_p$ is the diameter of the artery on the proximal side of the stenosis, $A_m$ is the minimum lumen area of the stenosis, $C_2 = 0.45$.

The flow-dependent component of $R_s$ in Eq. 9 includes losses due to flow separation and recirculation at the exit of narrowed regions of the artery. At high flow rates and in vessels with highly irregular cross sections, the effective resistance of a blood vessel can significantly exceed that predicted by Poiseuille's law, which is based on analysis of laminar flow of a Newtonian fluid through a straight cylinder. According to Kirkeeide:

$$k_e = \frac{C_3 \rho}{2} \left( \frac{1}{A_m} - \frac{1}{A_d} \right)^2 \tag{12}$$

where $\rho$ is the mass density of the blood, $A_d$ is the area of the artery distal to the stenosis, and $$C_3 = 1.21 + 0.08 \frac{\ell_s}{d_d}, \tag{13}$$

Here $\ell_s$ is the length of the stenosis, defined as the region between the wall angle inflection points on either side of the stenosis (FIG. 14), and $d_d$ is the diameter of the artery on the distal side of the stenosis. This equation accounts for the increase in expansion losses with lesion length.

Now that all of the terms in Eq. 9 have been defined, the vascular resistance ratio can be expressed as $$VRR = \frac{R_s}{R_s + R_e + R_{mv}} \tag{14}$$
$$= \frac{R_p + R_v + k_e Q}{R' + k_e Q}$$

with $$R' = R_e + R_{mv} + R_p + R_v \tag{15a}$$

and $$Q = \frac{\sqrt{R'^2 + 4k_e(P_a - P_v)} - R'}{2k_e} \tag{15b}$$

Figure 13:
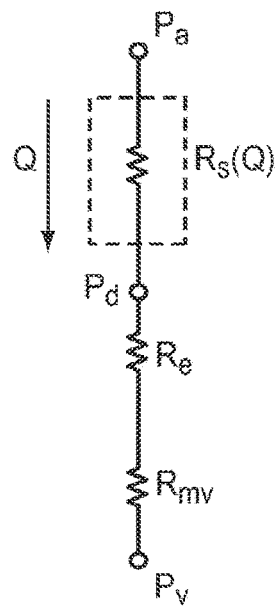
FIG. 13 is a lumped parameter model of the blood flow resistances in a portion of a coronary artery.

The other embodiments of the method, instead of Kirkeedee's equations, use a numerical Navier-Stokes solver such as FloWorks, (SolidWorks Corporation, Concord, Mass.) or Fluent (Ansys, Ann Arbor, Mich.) or equivalent to calculate the stenotic resistance $R_s$ in the model in FIG. 13. The vessel contours are delineated by OCT and the flow within the walls is broken into thousands of small volumes. Simultaneously, at each volume, the Navier-Stokes momentum and conservation of mass equations are solved to compute the flow field through the volume. From this flow field the pressure drop along the vessel is found.

Figure 15:
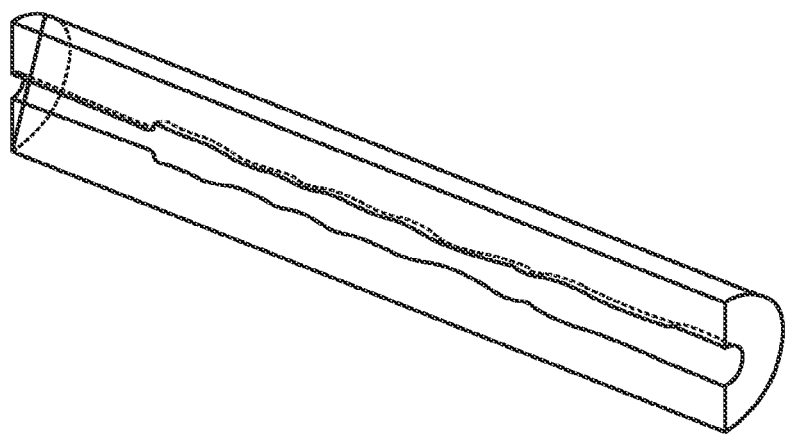
FIG. 15 is an example of cylindrically symmetric computational flow geometry on which a second embodiment of the invention is based.
Figure 16:
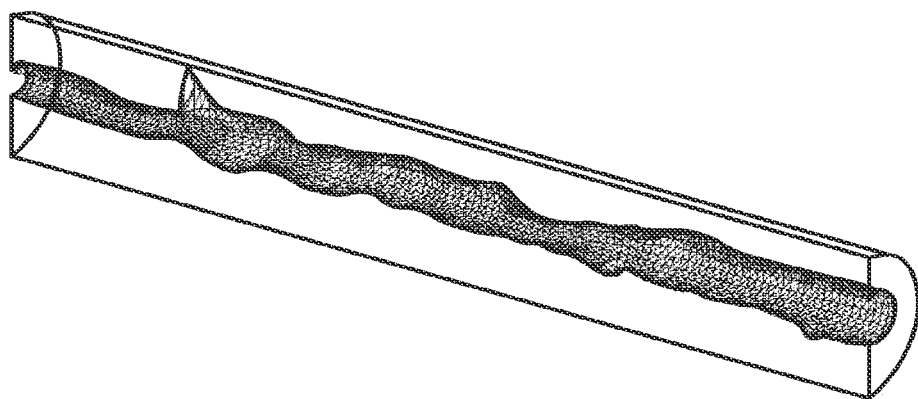
FIG. 16 is an example of a full 3D computational flow geometry on which a third embodiment of the invention is based.

In the second embodiment of the method, the cylindrically symmetrical computational flow model, the same area—versus-position graphs are used as in the first embodiment. The Navier-Stokes equations are solved assuming the shape is a perfect circle at each location along the OCT image. In the third embodiment, the full-3D computational flow model based on the actual OCT lumen contours is used. The wall geometry is broken into triangles spanning every other frame and every 15° around the catheter. FIGS. 15 and 16 show sections of the geometry on which blood flow is modeled.

Studies of anatomy show that the sum of the cross sectional area of branches derived from a parent is greater than the cross sectional area of the parent. This minimizes viscous shear stress through the epicardial tree. Based on viscous losses, Murray's law states that the cube of the radius of a parent vessel equals the sum of the cubes of the radii of the daughters. Table 2 shows the area increase calculated by Murray's law when the branches are symmetric.

The steps to obtain the branch sizes are:

The parent vessel area is taken as the proximal area at the reference plane. One daughter vessel is taken as the distal reference plane. The initial guess of the remaining daughter vessel areas is taken from an algorithm that interrogates the OCT image. The radius of the vessels is calculated, assuming they are circular. These radii are all multiplied by a single scale factor. The scale factor is determined by Murray's law. Murray's law is applied one branch at a time. The area remaining after the most proximal branch area is subtracted is used as the parent area for the next branch. The remaining area after Murray's law is applied to the last branch will equal the distal reference area.

With the cylindrically symmetric computational flow model, the flow outside of the imaged area is not calculated, but instead is calculated using the resistance network shown in FIG. 13. $R_s(Q)$ is calculated numerically with the computational flow simulation program with $R_e$ and $R_{mv}$ calculated in the same way as in the first embodiment of the method. $R_e$ and $R_{mv}$ are both independent of flow (i.e., produce a pressure drop linear with flow). They are simply added as a single resistor to the numerical simulation. The numerical flow simulator automatically adjusts the flow to maintain $P_v - P_a$.

The reference area, $A_n$ in Eqn. 5, is calculated differently for the two models. The cylindrically symmetric model (second method) does not have any branches, therefore $A_n$ is calculated based on the average of proximal and distal areas. Thus, the velocity in the FloWorks geometry will be an average of the flows that would be encountered through the tapering section. The full 3-D model (third embodiment) includes branches, therefore $A_n$ is calculated based on the proximal area only.

Figure 24:
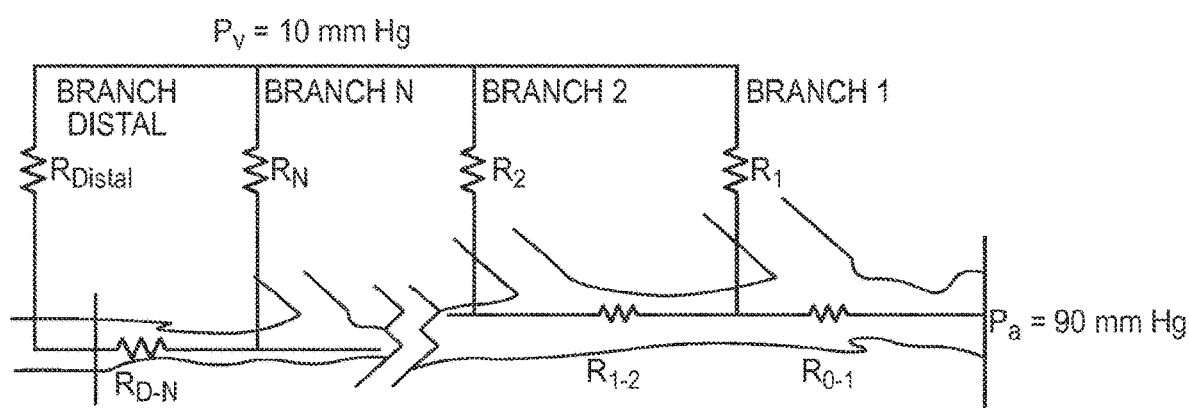
FIG. 24 depicts a schematic diagram of an equivalent resistor network of the pressure drops through the artery according to an illustrative embodiment of the invention.

The lumped resistor method shown in FIG. 13 is extended for the full 3-D Computational Flow Model in FIG. 24. The resistance of the branches $R_1, R_2 \ldots R_N$ and $R_{Distal}$ are each composed of the series resistors $R_e + R_{mv}$. The downstream end of every branch resistor is at $P_v$ (10 mm Hg). The upstream end of the resistor is at the static pressure that numerical method calculates at that branch. The input pressure of the parent artery at the proximal reference is 90 mm Hg.

$R_e$ of each branch is calculated based on the location in the image. Calculation of $R_{mv}$ is more complex. According to Murray's law, the sum of the cross-sectional areas of branches coming off a parent is greater than the cross sectional area of the parent. Consequently, the velocity decreases after every branch. This affects $R_{mv}$ for the entire artery and for each branch.

$R_{mv}$ for the entire artery is adjusted by assuming the 1.0 mm Hg cm$^{-1}$s value of h-MRv was determined based on a reference diameter of 3.4 mm. For other proximal reference diameters $R_{mv}$ is adjusted downwards according to the ratio of the proximal reference diameter to the reference diameter to the ¼ power. The ¼ power equates pressure drops through the vasculature. Data on the variation of velocity data through the coronaries is limited, but the ¼ power rule seems to correlate the published data as shown in Table 3. A more sophisticated approach would adjust $R_{mv}$ according to the vessel type (LAD: left anterior descending artery, RCA: right coronary artery, LCx: left circumflex).

Likewise, $R_{mv}$ for each branch is adjusted by the same ¼ power of the diameter ratio of the branches to the reference diameter of 3.4 mm. If a branch is smaller than 2 mm, $R_{mv}$ is taken at 2 mm diameter. $R_{mv}$ for all the daughter branches is summed to insure it adds up to $R_{mv}$ for the proximal reference. If it is different, $R_{mv}$ for all the branches are scaled equally.

As the numerical program is run, the pressure and flow are obtained along the artery length. The slope of the total pressure along the length can be used to highlight areas of high resistance. The static pressure along the length can be correlated with pressure measurements. VRR is calculated between any two points of interest, usually the distal and proximal references. Since the flow is calculated, other indices that use flow and pressure, such as Stenotic Reserve Index (SRI) can be calculated. Meuwissen et al. defined the Stenosis Resistance Index (SRI) as the slope of this line between two measurement points:

$SRI$ = Pressure Difference Between Measurement Points $(dP)$/Proximal Velocity

In one embodiment, SRI is calculated by assuming a velocity. Velocity is fairly constant in human arteries. In one study of 32 patients after percutaneous coronary intervention PCI, the measured velocity was 79±17.2 cm/s. Since the velocity variation is small and the SRI curve is fairly independent of velocity, the estimate of SRI made without velocity measurements can be acceptable.

Velocity is a better way to normalize SRI than flow because pressure drop is mostly proportional to velocity. If flow is used, it typically underestimates the effect of a stenosis in a large vessel and conversely overestimates the effect of a stenosis in a small vessel. The velocity that is selected is the velocity at a reference diameter, not the stenosis velocity. The physician selects the proximal reference and the velocity measurement is taken there. The resulting SRI will give the physician the resistance that will be eliminated by the stent.

The flow through the region of interest will change if a side branch is detected. The flow down the side branch will be estimated from the side branch size and the reduction in area from the proximal to distal reference. Both the algebraic equations and the Navier-Stokes Equation are modified to include the side branches.

If SRI is reported, a different SRI will be used than that of Meuwissen et al. This index, termed the LightLab SRI (LSRI) is defined as:

$LSRI$ = Total Pressure Difference/Velocity – Integrated Poiseuille Equation where: total pressure difference is the static pressure at a first location plus the velocity head ($\rho V_1^2/2$) at the first location minus the static pressure at a second location plus the velocity head ($\rho V_2^2/2$) at the second location. The locations typically straddle the region of interest in the lumen. Velocity, V, is the bulk average velocity. The integrated Poiseuille equation is the laminar flow pressure drop calculated between the reference locations assuming the diameter increases linearly. This is an improvement over the standard SRI measurement because the total pressure is more reflective of the true losses in an artery than the static pressure used in standard SRI and the integrated Poiseuille equation removes the effects of the distance between measurement locations, which is a limitation of standard SRI.

Another parameter that is measurable by this technique is the fractional flow reserve (FFR). As defined by the model in FIG. 13, the vascular resistance ratio (VRR) has a direct relationship with the fractional flow reserve (FFR). The FFR is determined from measurements of the pressure distal to a stenosis relative to the arterial pressure:

$$FFR = \frac{P_d - P_v}{P_a - P_v} \quad (16)$$

Clinically an FFR value greater than or equal to 0.75 typically is considered to mean that treatment is not required. Generally the FFR is measured following the administration of drugs that cause a maximum hyperemic response by causing the capillary beds to dilate followed by the taking of an intravenous pressure measurement.

Assuming that there are no additional stenoses proximal to the stenotic segment, VRR is inversely proportional to FFR:

$$VRR = \frac{R_s}{R_T} = \frac{(P_a - P_d)/Q}{(P_a - P_v)/Q} = \frac{(P_a - P_d)}{(P_a - P_v)} = 1 - FFR \quad (17)$$

A VRR of less than 0.25 means that treatment is not indicated. A benefit of VRR is that, as shown below, a VRR calculation may be made without the use of drugs or the measurement of intravascular pressure.

Figure 17:
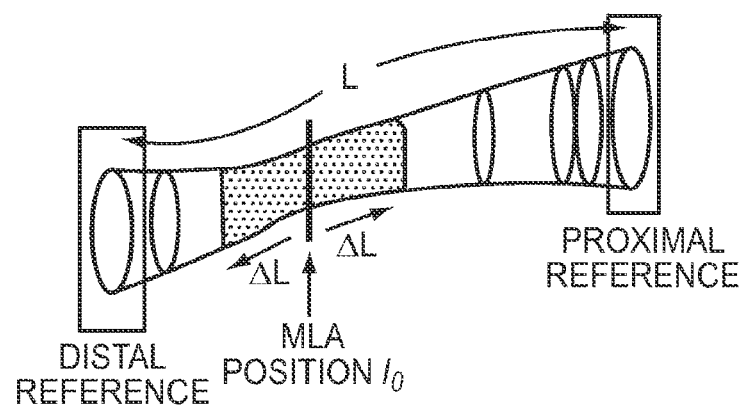
FIG. 17 is an example of a 3D display in which the contiguous length of an artery that encompasses a fixed fraction of the total resistance between user-adjustable proximal and distal reference planes is highlighted.
Figure 18:
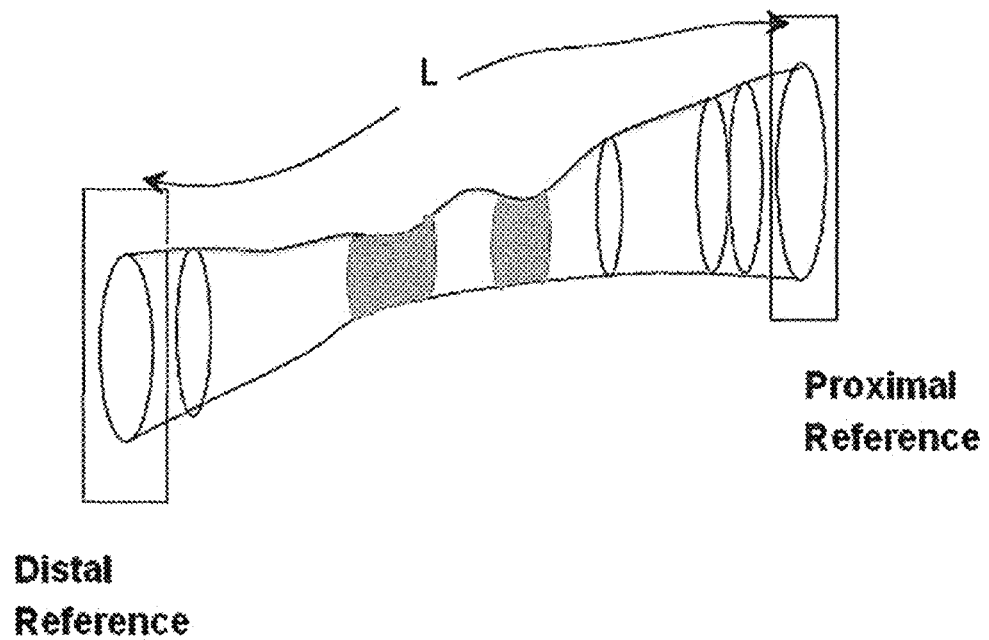
FIG. 18 is an example of a 3D display in which all incremental segments of the artery that encompasses a fixed fraction of the total resistance between user-adjustable proximal and distal reference planes are highlighted.

Once the segmental resistances on which the VRR is based have been calculated, additional information can be displayed to help the clinician select the length of a stent required to cover a stenotic lesion. One concept for displaying this information is illustrated in FIG. 17. Here, to provide feedback about the lesion length, the segment of the artery centered on the MLA plane that encompasses a user-selectable fraction κ (typically 0.9≤κ≤0.95) of the total vascular resistance is highlighted. In mathematical terms, the length of the highlighted region, 2ΔL, centered on the MLA position $\ell_0$ is determined such that the relationship $$\sum_{N(\ell_0-\Delta L)}^{N(\ell_0+\Delta L)} R_i \geq \kappa R_m \tag{18}$$

is satisfied. Here $N(\ell_0-\Delta L)$ and $N(\ell_0+\Delta L)$ are the frame numbers at the distal and proximal limits of the vessel segment. Alternatively, the high-resistance regions can be identified independently of the location of the MLA cross section by sorting the resistances of the incremental segments from highest to lowest and highlighting only those segments at the top of the list that sum to a user-selectable fraction of the total vascular resistance. The advantage of this method is that more than one region of high resistance in a diffusely narrowed artery can be identified readily, as shown by the example in FIG. 18.

Once the parameters of vessel size and blood flow resistance are calculated, the present invention also provides methods for optimizing stent choice and placement automatically or semi-automatically via interactive commands. These flow calculations, when combined with a set of a priori constraints, enable a cardiologist to optimize the length, diameter, and longitudinal position of a stent before implantation.

Figure 19A:
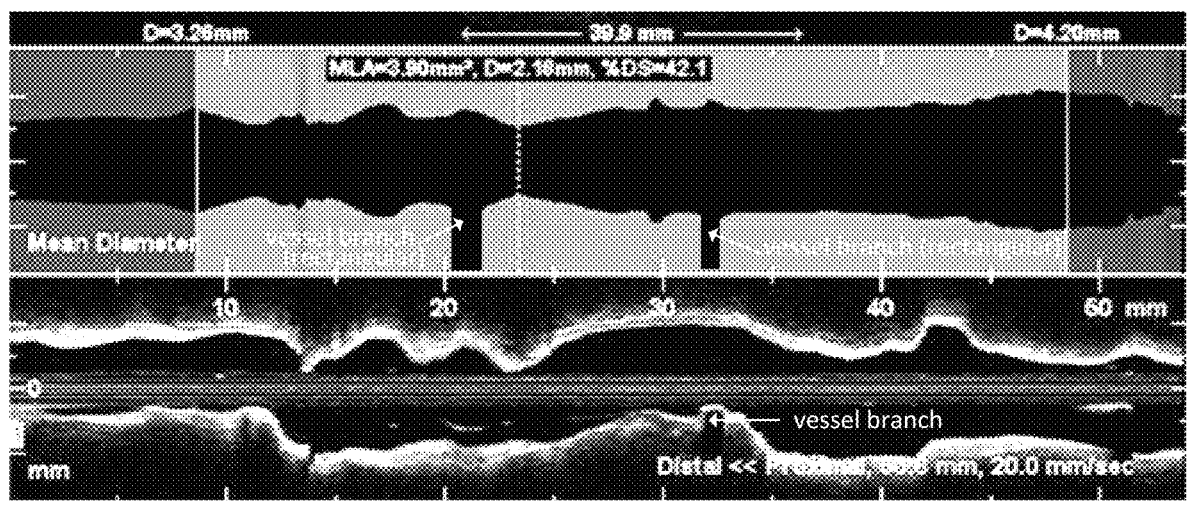
FIGS. 19a and 19b are examples of embodiments of a longitudinal display of the mean diameter of a coronary artery in which the arterial branches are shown as rectangular protrusions with widths proportional to the diameters of the ostia of the branches and as circular regions with diameters proportional to the diameters of the ostia of the branches, respectively.
Figure 19B:
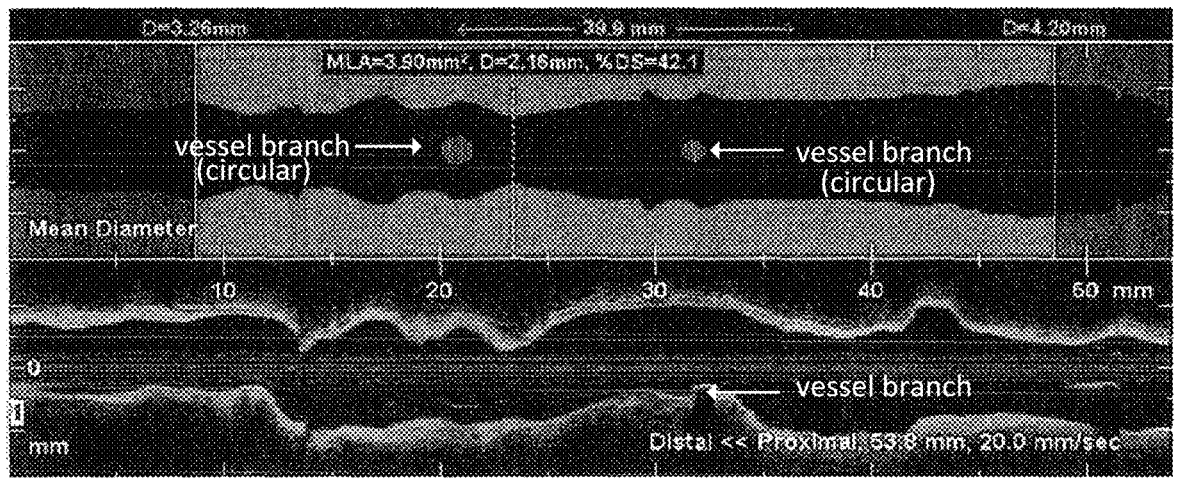

Referring again to FIG. 5, a three-dimensional (3D) image of the lumen of a coronary artery derived from OCT image data is depicted. To generate this image, the contours of the wall of the lumen are traced automatically by computer software described above. The morphological data represented by the three-dimensional image of the lumen provide the starting point for various embodiments of the stent optimization procedure. The first image-processing step reduces the 3D data set to a cylindrically symmetrical data set that shows the mean diameter of each cross section along the axis of the catheter. The mean diameter D at each longitudinal position x is calculated as the diameter of a circle with the same area as the cross-section, $$D(x) = 2\sqrt{\frac{A(x)}{\pi}} \tag{19}$$

where A(x) is the area of the cross section. Alternatively, the mean diameter can be found by averaging the lengths of chords drawn through the centroid of the lumen cross section. FIGS. 19a and 19b show examples of displays of mean-diameter for an OCT image of a coronary artery. In FIG. 19a, the branches of the artery are shown as perpendicular bars with widths equal to the widths of the ostia of the branches, while in FIG. 19b, the vessel branches are shown as circles with diameters to the widths of the ostia of the branches.

Figure 20:
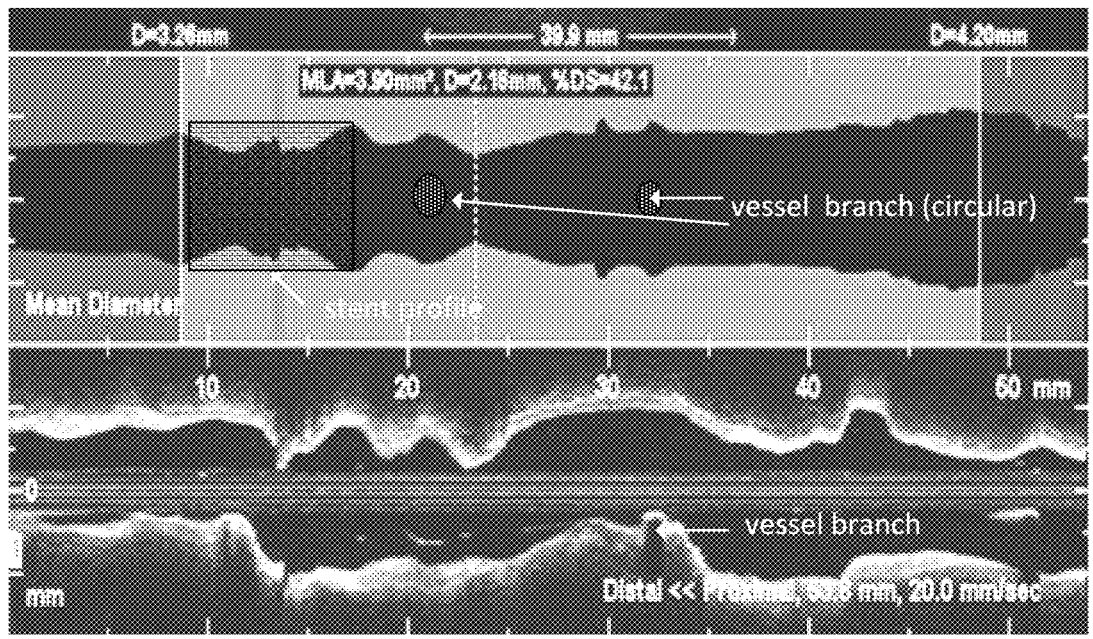
FIG. 20 is an example of an embodiment of a longitudinal display of the mean diameter of a coronary artery that includes the profile of a superimposed stent.

For interactive stent optimization, the mean-diameter display shows the position of a reconfigurable stent superimposed on the vessel profile, as illustrated in FIG. 20. The expanded diameter, length, and longitudinal position of the stent are the main variables that determine the effectiveness of the stent in restoring the available blood flow to the heart muscle. The present invention employs the difference between the calculated values of the vascular resistance ratio (VRR) before and after stenting as a key stent optimization parameter. Another important optimization parameter is the maximum stent malapposition distance, defined as the widest separation between the surface of the stent struts and the vessel wall over the entire length of the stent. Minimization of this distance, especially for drug-eluting stents, is necessary to assure that the stent is affixed firmly to the vessel wall and that the stent provides adequate radial support to prevent collapse of the vessel. A third important optimization parameter is the degree of overlap of the stent and the ostia of side branches. Minimal overlap is desirable to avoid blockage of blood flow to branches as a result of thrombus formation or growth of new tissue on the stent struts.

Figure 21:
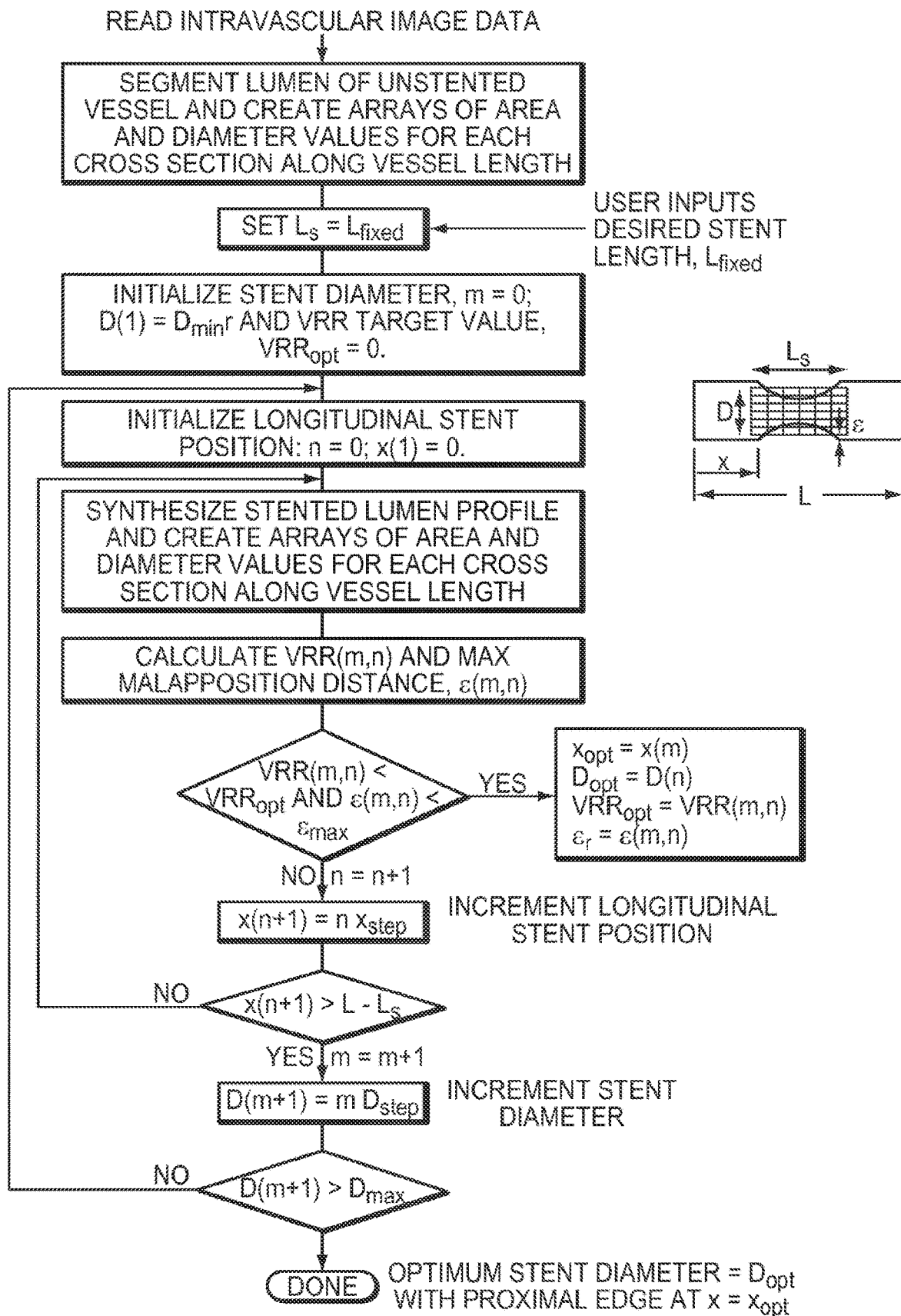
FIG. 21 is a flow diagram of an embodiment of a method for stent diameter and position optimization based on a user-selected stent length.

The various embodiments of the present invention provide methods for choosing the optimal stent length, diameter, and longitudinal position in accordance with the aforementioned optimization parameters (VRR, malapposition distance, branch overlap, presence of calcium, etc.). The flow chart in FIG. 21 outlines the optimization procedure associated with one specific embodiment. In this embodiment, the user chooses a desired stent length, $L_{fixed}$, and the optimization proceeds iteratively to find the longitudinal position of the stent, $x_{opt}$, and diameter of the stent, $D_{opt}$, that minimizes VRR while maintaining a malapposition distance, ε, less than a maximum allowable distance, $\varepsilon_{max}$, and a stent diameter less than $D_{max}$. Typically $\varepsilon_{max}$ is fixed at a small value between 0 and a value deemed clinically insignificant (e.g., 0.1 mm) and $D_{max}$ is set equal to the maximum diameter of the vessel measured within the imaged segment plus one stent diameter increment (typically 0.25 mm). To accelerate the iteration, the sets of available stent diameters $\{D_{min} \leq D \leq D_{max}\}$ and stent diameters and stent positions $\{0 \leq x \leq (L-L_{fixed})\}$ are limited to discrete values separated by clinically significant increments. Further acceleration of the optimization can be achieved by employing a multivariate look-up table of stent diameters and stent positions instead of linear arrays of variables. Although not shown in flow chart in FIG. 21, additional constraints, such as the degree of overlap with side branches and calcified regions, are included within the scope of the invention.

In addition to reporting the recommended diameter and position of the stent to the user, this specific embodiment of the optimization procedure also reports the predicted values of $VRR_{opt}$, the vascular resistance ratio, and $\varepsilon_r$, the residual malapposition distance. If the user deems these values to be unsatisfactory, the optimization can be repeated with a longer stent length as an input. In this way, errors in the sizing and positioning of stents can be avoided before implantation.

Figure 22:
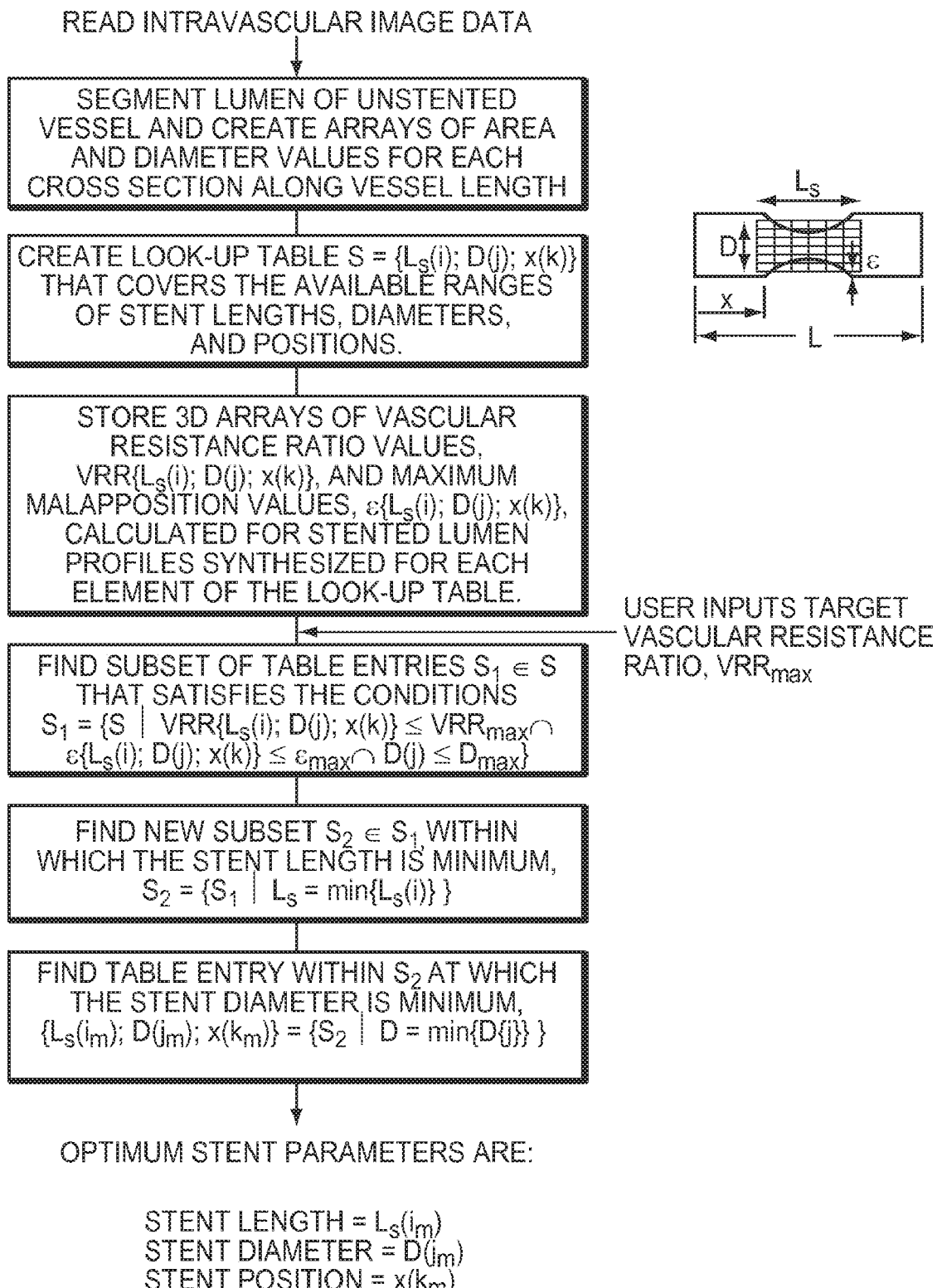
FIG. 22 is a flow diagram of an embodiment of a method for stent diameter, length, and position optimization based on a user-selected maximum value of the post-stent VRR.

FIG. 22 outlines the steps of an embodiment of a fully automatic optimization procedure in which the diameter, length, and longitudinal position are optimized simultaneously. Here the user inputs only a target VRR value, $VRR_{max}$, and the optimization then proceeds iteratively to find the shortest stent that achieves the desired blood flow resistance under the constraints imposed on maximum diameter and maximum malapposition distance.

In more detail, the system first creates arrays of area and diameter for each cross-section along the unstented vessel. Next, the system creates a lookup table that has the available ranges of stent diameter, length and position. Then, progressing through each entry in the lookup table, the system calculates the VRR and maximum malapposition value. The maximum malapposition value equals the distance between the maximum unstented diameter in the segment and the diameter of the stent. Table entries that result in VRR values less than $VRR_{max}$ and the maximum malapposition values are retained and then the stent length for each subset is determined. The table entry in which the stent length is a minimum defines the optimal stent parameters.

To be useful as an interactive bed side tool, the recalculation of VRR for a selected stent size needs to be almost instantaneous. The most accurate method to find the chosen stent effect of VRR would be to first measure or calculate VRR on the unstented artery using the OCT measurements above or a finite element computational fluid dynamics program and then recalculate VRR using the same finite element computational fluid dynamics program on the proposed stented artery shape. However, most computational fluid dynamics programs will not run fast enough on typical computers to quickly show the affect of the proposed stent. A method is needed to have the accuracy of computational fluid dynamics but allow the rapid recalculation of VRR with the proposed placement of a stent.

A hybrid approach is disclosed here that allows for rapid recalculation. In the region of the proposed stent, algebraic equations are used to determine pressure drop. In the regions outside of the stent, the previously obtained measured or computational fluid dynamics solution is used, modified by the effect of the stent. The rapid recalculation is obtained by only using algebraic equations during the stent sizing. Once the stent sizing is complete, a full computational fluid dynamics simulation may be run to obtain an even more accurate answer.

The initial calculation of VRR on the unstented artery is done using a finite element computational fluid dynamics program. Since there is some time between the end of the imaging procedure and the start of the stent placement, the amount of time this calculation takes is not a limiting constraint. An important output of the computational fluid dynamics program is a total pressure versus distance graph as shown in the FIG. 23. The simplest way to calculate the change in VRR from the proposed stent addition is simply to subtract the pressure drop in the stented area as shown. The VRR display is updated as the stent length and location are changed by the operator.

Figure 23:
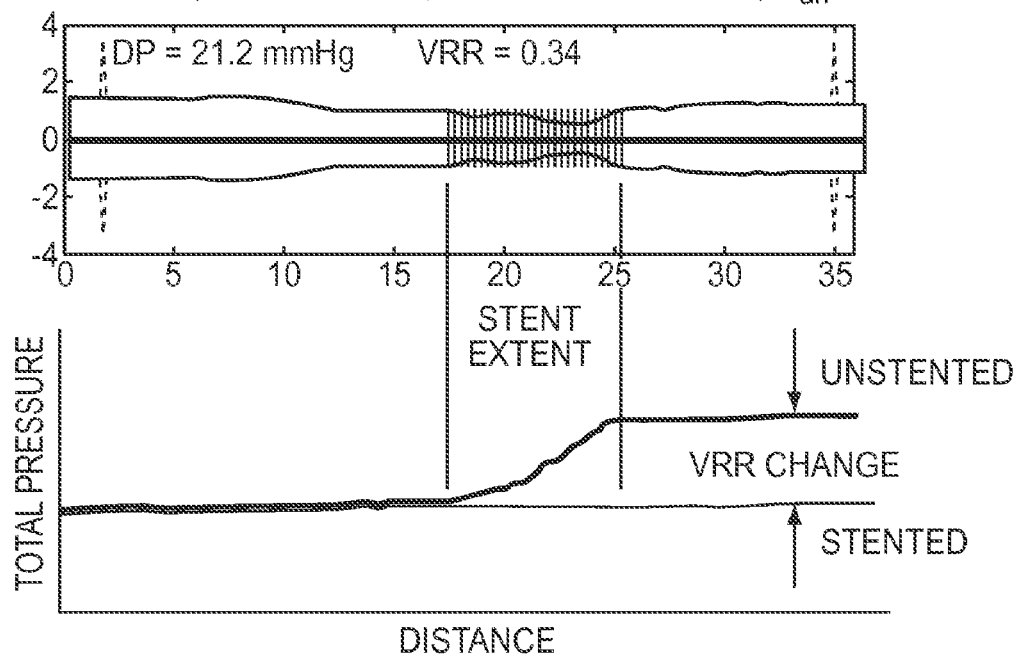
FIG. 23 is an example of a total pressure versus distance graph as produced by a calculation method using fluid dynamics according to an illustrative embodiment of the invention.

A more sophisticated approach takes into account that the pressure drop outside of the proposed stented area will increase because the flow increases with the elimination of the stenosis. FIG. 24 shows an equivalent resistor network model of the pressure drops through the artery. The total pressure drop graph from FIG. 23 is broken up into equivalent flow resistors, each spanning a branch or the artery. $R_{0-1}$ is the flow resistance from the proximal end of the OCT image to the first branch, $R_{1-2}$ is between the first and second branches, and $R_{D-N}$ is between the last branch and the distal end of the OCT scan. If a stent is placed in one of the resistors, the pressure drop in that resistor is modified as follows. First, the calculated pressure drop from the stenosis is set to zero in the stent. The Poiseuille pressure drop through the length of the stent is added and the losses at the entrance and exit of the stent due to the diameter change are added. The flow calculated with the stenosis by computational fluid dynamics is used to set the resistor values.

The resistor network in FIG. 24 can be solved by using equations for resistors in series and parallel. An explicit series of equations for flow and thus pressure drop in the stented artery can then be found. The flow division between the branches is readjusted from the resistor network. The flow resistances may be considered linear with flow as a first approximation. A more sophisticated approximation will include the non-linear response of pressure drop with flow. The new value of VRR is displayed on the screen as the stent is resized. This calculation happens rapidly as it is simply algebraic equations. This value of VRR is marked as preliminary. The full computational fluid dynamics simulation takes place during the stent resizing and when the calculation is complete the VRR value is marked as final.

Target values of VRR can be established according to results of published clinical studies. For example, the results of one influential study showed that adverse event rates in patients with a single stented lesion were reduced significantly when the fractional flow reserve (FFR) measured in the stented artery was in the range 0.96-1.0 compared to the adverse event rates of a similar population of patients with measured FFR values in the range 0.9-0.95. Therefore, $FFR_{min}=0.96$ is a post-stent target supported by clinical evidence. According to its definition, VRR has a simple inverse relationship with fractional flow reserve (VRR=1−FFR); it follows that, based on this study, an appropriate target maximum value of is $VRR_{max}=1-0.96=0.04$.

FIGS. 25 and 26 depict the output results of the specific embodiments of the invention. FIGS. 25a and 25b show the pre- and (predicted) post-stented mean-diameter lumen profiles resulting from the fixed-stent-length optimization procedure for two different stent lengths, $L_{fixed}=8$ mm and $L_{fixed}=24$ mm. The input data were derived from a sequence of OCT images that was recorded in vivo from a branch of a patient's coronary artery. In this example, the optimization procedure determined the diameters and longitudinal positions of the stents that minimized the hyperemic blood flow resistance, while maintaining good stent apposition. The predicted residual gaps between the stent and the vessel wall for $L_{fixed}=24$ mm are shown in FIG. 26 as blank regions FIGS. 26a and 26b show the pre- and (predicted) post-stented mean-diameter lumen profiles resulting from the fully automatic optimization procedure for two different target VRR values, $VRR_{max} \leq 0.05$ and $VRR_{max} \leq 0.02$. Again, the input data were derived from a sequence of OCT images recorded in vivo from a branch of a patient's coronary artery. The procedure determined the longitudinal positions, diameters, and minimum lengths of the stents required to reduce VRR below the target values, while maintaining good apposition between the stent and the vessel wall.

Figure 27:
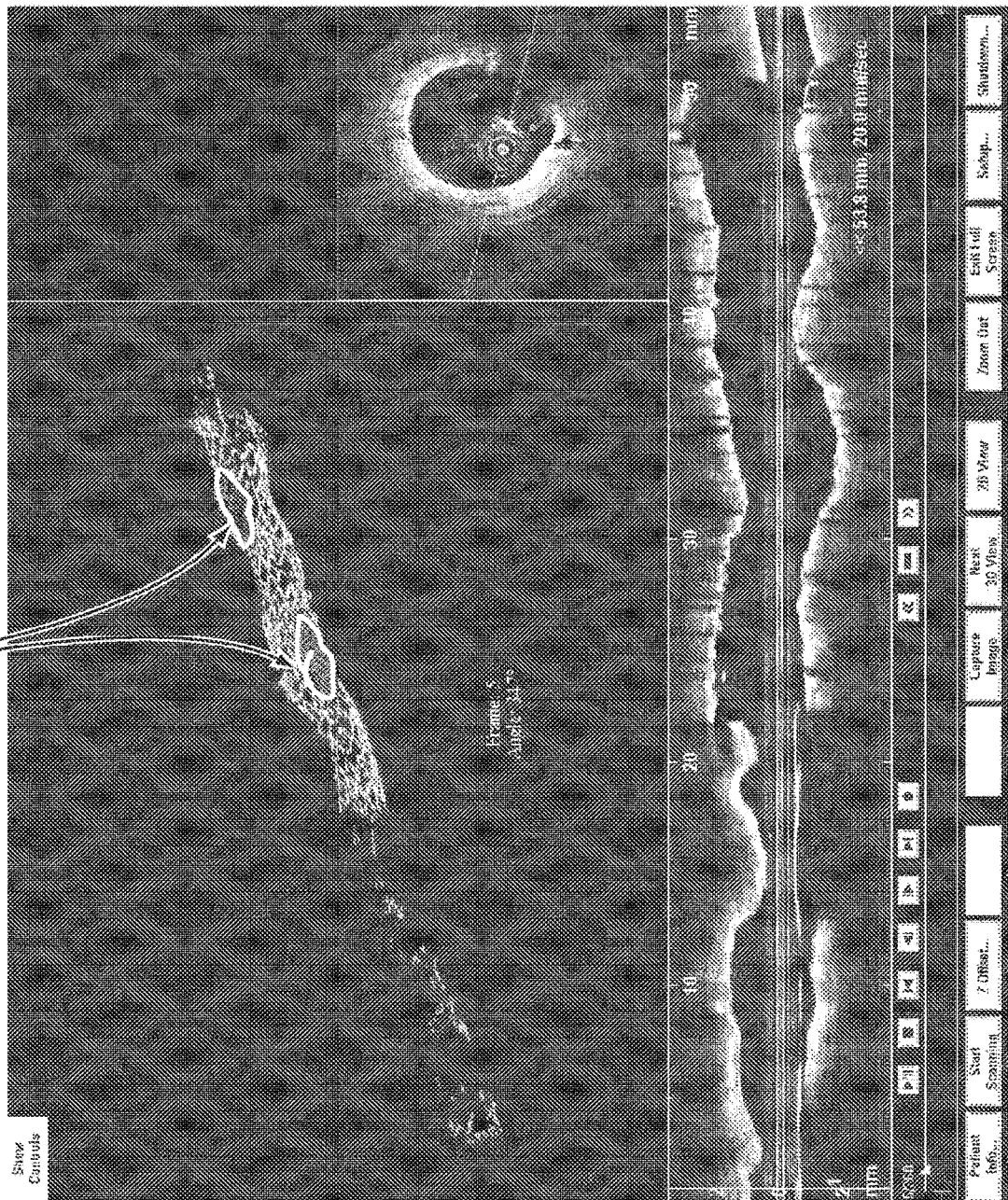
FIG. 27 is a software-based user interface showing a longitudinal OCT image in the bottom, a cross sectional view on the right, and the degree of stent malapposition in three dimensions in the top according to an illustrative embodiment of the invention.

FIG. 27 shows a computer interface with a three dimensional depiction in the top panel of a stent that is not properly placed in the lumen of interest. Two regions of stent malapposition are shown as hatched regions. Thus, in one embodiment, the methods of the invention and features described herein are directed to a computer-based user interface that allows views of OCT in multiple panels. Further, stent malapposition can be shown in three-dimensions. In addition, in the case of stimulated stent placement, the user may reposition the stent to remove the areas of malapposition to simulate proper stent placement prior to implanting a stent in a real patient The present invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, histology images, OCT images, vascular resistance, overlays masks, signal processing, weighting artifact removal, contour detection and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, clock signals, region of interest types, formulas, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

TABLE 1

| Reference vessel | Balloon | Stented lesion | Upsize stented lesion |
|---|---|---|---|
| 1.73 ± 0.38 (n = 20) | 1.72 ± 0.53 (n = 19) | 1.58 ± 0.61 (n = 24) | 1.32 ± 0.39 (n = 11) |
| 1.75 ± 0.37 (n = 13) | 1.59 ± 0.38 (n = 12) | 1.49 ± 0.41 (n = 15) | 1.29 ± 0.40 (n = 10) |
|  |  | 1.52 ± 0.40 (n = 10) |  |
| 1.82 ± 0.44 (n = 23) |  | 1.67 ± 0.73 (n = 29) |  |

TABLE 2

Area Increase After a Branch

| Bifurcation Area Increase | Trifurcations | Angiography Study |
|---|---|---|
| 1.214 (n = 12) |  | Patients without coronary artery disease |
| 1.30 (n = 20) | 1.12 | Left main of patients without coronary disease |
| 1.26 | 1.44 | N/A |

TABLE 3

|  | Proximal End of Artery | | | Distal End of Artery | | |
|---|---|---|---|---|---|---|
|  | LAD | LCx | RCA | LAD | LCx | RCA |
| Peak Velocity (cm/s) | 104 | 79 | 72 | 70 | 71 | 67 |
| Diameter (mm) | 3.5 | 3.1 | 3.4 | 2 | 2 | 2 |
| Peak Vel/67 | 1.55 | 1.18 | 1.07 | 1.04 | 1.06 | 1.00 |
| V/D^0.25/56.5 | 1.35 | 1.05 | 0.94 | 1.04 | 1.06 | 1.00 |

The invention claimed is:

1. A method for identifying effect of stenotic lesions within a vessel, comprising:
   receiving, by one or more processors, vessel image data of the vessel;
   generating, by the one or more processors, a blood flow model of the vessel based on the vessel image data, wherein the blood flow model identifies a size and location of branch vessels extending from the vessel;
   calculating, by the one or more processors, values relating to available blood flow along the vessel based on the blood flow model;
   identifying, by the one or more processors, one or more stenotic lesions within the vessel;
   providing for display, by the one or more processors, a representation of the vessel that includes an indication of the one or more stenotic lesions within the vessel with a representation of changes in ratios of available blood flow along lengths of the vessel proximate and distal to the one or more stenotic lesions.

2. The method of claim 1, wherein calculating values relating to available blood flow along the vessel comprises determining a ratio quantifying hemodynamic values across a segment.

3. The method of claim 2, further comprising determining, by the one or more processors, whether the ratio exceeds a predetermined threshold.

4. The method of claim 3, further comprising indicating, by the one or more processors, a treatment when the ratio exceeds the predetermined threshold.

5. The method of claim 3, further comprising not indicating a treatment when the ratio does not meet the predetermined threshold.

6. The method of claim 3, wherein the ratio is a vascular resistance ratio, and the predetermined threshold is 0.25.

7. The method of claim 1, further comprising identifying, by the one or more processors, stenting for the stenotic lesion based on one or more stenting parameters.

8. The method of claim 7, wherein the one or more stenting parameters include a presence of calcium.

9. The method of claim 1, further comprising:
   receiving, by the one or more processors, user input in connection with a 3D representation of the vessel identifying a proximal location and a distal location relative to the stenotic lesion;
   altering, by the one or more processors, the blood flow model to simulate widening of the vessel between the proximal location and the distal location;
   calculating, by the one or more processors, updated values relating to the available blood flow along the vessel based on the altered blood flow model; and
   providing for display one or more updated ratios of available blood flow.

10. A system for identifying effect of stenotic lesions within a vessel, comprising:
    memory;
    one or more processors in communication the memory, the one or more processors configured to:
      receive vessel image data of the vessel;
      generate a blood flow model of the vessel based on the vessel image data, wherein the blood flow model identifies a size and location of branch vessels extending from the vessel;
      calculate values relating to available blood flow along the vessel based on the resistance model;
      identify one or more stenotic lesions within the vessel;
      provide for display a representation of the vessel that includes an indication of the one or more stenotic lesions within the vessel, with a representation of changes in ratios of available blood flow along lengths of the vessel proximate and distal to the one or more stenotic lesions.

11. The system of claim 10, wherein calculating the values relating the available blood flow along the vessel comprises determining a ratio quantifying hemodynamic values across a segment.

12. The system of claim 11, wherein the one or more processors are further configured to determine whether the ratio exceeds a predetermined threshold.

13. The system of claim 12, wherein the one or more processors are further configured to indicate a treatment when the ratio exceeds the predetermined threshold.

14. The system of claim 12, wherein the one or more processors are further configured to not indicate a treatment when the ratio does not meet the predetermined threshold.

15. The system of claim 12, wherein the ratio is a vascular resistance ratio, and the predetermined threshold is 0.25.

16. The system of claim 10, wherein the one or more processors are further configured to identify stenting for the stenotic lesion based on one or more stenting parameters.

17. The system of claim 16, wherein the one or more stenting parameters include a presence of calcium.

18. The system of claim 10, further comprising:
receiving user input in connection with a 3D representation of the vessel identifying a proximal location and a distal location relative to the stenotic lesion;
altering the blood flow model to simulate widening of the vessel between the proximal location and the distal location;
calculating updated values relating to the available blood flow along the vessel based on the altered blood flow model; and
providing for display one or more updated ratios of available blood flow.

19. A non-transitory computer-readable medium storing instructions executable by one or more processors for performing a method of identifying effect of stenotic lesions within a vessel, comprising:
receiving vessel image data of the vessel;
generating a blood flow model of the vessel based on the vessel image data, wherein the blood flow model identifies a size and location of branch vessels extending from the vessel;
calculating values relating to available blood flow along the vessel based on the resistance model;
identifying one or more stenotic lesions within the vessel;
providing for display a representation of the vessel that includes an indication of the one or more stenotic lesions within the vessel, with a representation of changes in ratios of available blood flow along lengths of the vessel proximate and distal to the one or more stenotic lesions.

20. The non-transitory computer-readable medium of claim 15, further comprising:
receiving user input in connection with a 3D representation of the vessel identifying a proximal location and a distal location relative to the stenotic lesion;
altering the blood flow model to simulate widening of the vessel between the proximal location and the distal location;
calculating updated values relating to the available blood flow along the vessel based on the altered blood flow model; and
providing for display one or more updated ratios of available blood flow.

21. The method of claim 1, wherein one or more of the lengths of the vessel spans one or more branch vessels extending from the vessel, and wherein the changes in the ratios of available blood flow along lengths of the vessel comprises a representation relating to a fractional flow reserve ratio, between a point proximate to one or more of the stenotic lesions and a point distal to one or more of the stenotic lesions.

22. The method of claim 1, wherein providing for display the representation of changes in the ratios of available blood flow along the vessel includes a display of changes in the ratios of available blood flow along the vessel when the vessel is not stented and a display of changes in the ratios of available blood flow along the vessel based on a simulation of a stent being placed within the vessel.

23. The system of claim 10, wherein one or more of the lengths of the vessel spans one or more branch vessels extending from the vessel, and wherein the changes in the ratios of available blood flow along the vessel comprises a representation relating to a fractional flow reserve ratio, between a point proximate to one or more of the stenotic lesions and a point distal to one or more of the stenotic lesions.

24. The system of claim 10, wherein providing for display the representation of changes in ratios of available blood flow along the vessel includes a display of changes in ratios of available blood flow along the vessel when the vessel is not stented and a display of changes in ratios of available blood flow along the vessel based on a simulation of a stent being placed within the vessel.

* * * * *